(12) United States Patent
Lindholm et al.

(10) Patent No.: US 7,186,811 B2
(45) Date of Patent: Mar. 6, 2007

(54) OSTEOGENIC DEVICE AND A METHOD FOR PREPARING THE DEVICE

(75) Inventors: Sam T. Lindholm, Espoo (FI); Aulis Marttinen, Tampere (FI)

(73) Assignee: Bioactive Bone Substitutes Oy, AB, Tampere (FI)

( * ) Notice: Subject to any disclaimer, the term of this patent is extended or adjusted under 35 U.S.C. 154(b) by 533 days.

(21) Appl. No.: 10/759,244

(22) Filed: Jan. 20, 2004

(65) Prior Publication Data

US 2005/0142164 A1 Jun. 30, 2005

Related U.S. Application Data

(62) Division of application No. 09/125,963, filed as application No. PCT/FI96/00118 on Feb. 29, 1996, now abandoned.

(51) Int. Cl.
*C07K 1/36* (2006.01)
*C07K 1/34* (2006.01)
*C07K 1/16* (2006.01)
*C07K 14/51* (2006.01)

(52) U.S. Cl. .................. 530/417; 530/414; 530/412; 530/840; 530/350

(58) Field of Classification Search .................. None
See application file for complete search history.

(56) References Cited

U.S. PATENT DOCUMENTS

| 4,294,753 A | 10/1981 | Urist |
|---|---|---|
| 4,434,094 A | 2/1984 | Seyedin et al. |
| 4,455,256 A | 6/1984 | Urist |
| 4,563,350 A | 1/1986 | Nathan et al. |
| 4,608,199 A | 8/1986 | Caplan et al. |
| 4,627,982 A | 12/1986 | Seyedin et al. |
| 4,681,763 A | 7/1987 | Nathanson et al. |

(Continued)

FOREIGN PATENT DOCUMENTS

DE    41 30 546    3/1993

(Continued)

OTHER PUBLICATIONS

Aono, Aki, et al., "Potent Ectopic Bone-Inducing Activity of Bone Morphogenetic Protein-4/7 Heterodimer," Biochemical and Biophysical Research Communication (1995), pp. 670-677, Academic Press, Inc.

(Continued)

*Primary Examiner*—David Romeo
(74) *Attorney, Agent, or Firm*—Buchanan, Ingersoll & Rooney, P.C.

(57) ABSTRACT

The present invention is related to an osteogenic device and its preparation. Said device comprises a bone morphogenetic protein (BMP), preferably a modified BMP complex obtainable by a modification of the conventional guanidum hydrochloride extraction method and collagens, preferably collagen I or collagen IV, impregnated in and/or adsorbed on a bioceramic carrier, preferably a shapable body (block) originating from a coral skeleton. The method of isolating said modified BMP complex which lacks an immunogenic component and consists essentially of a 100–700 kD and a 15–25 kD protein with osteoinductive properties and preferably of the 15–25 kD protein which has improved storage properties as well as its use in the osteogenic device with improved osteoinductive properties is also disclosed.

2 Claims, 3 Drawing Sheets

U.S. PATENT DOCUMENTS

Figure 1:
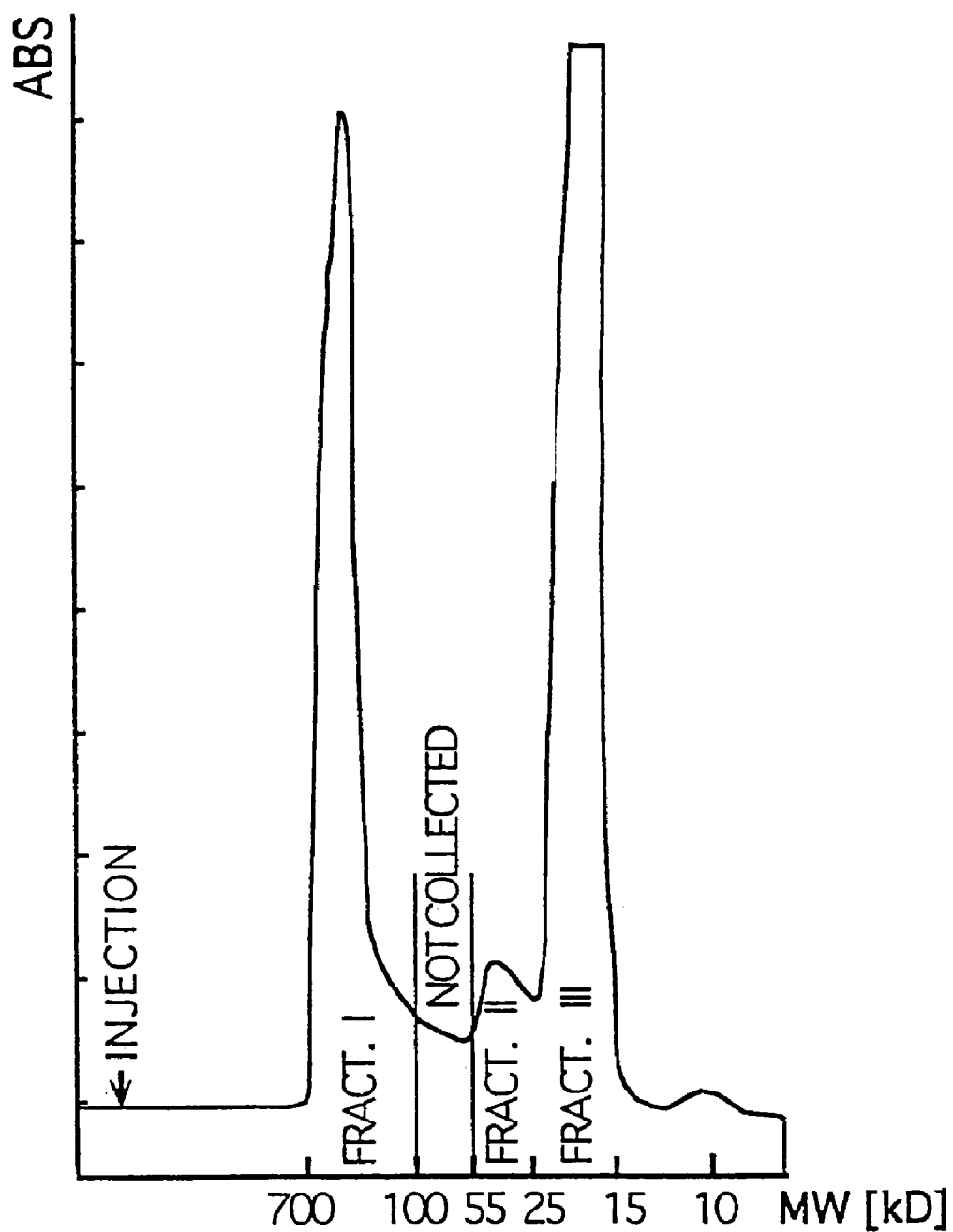

| | | | |
|---|---|---|---|
| 4,737,578 | A | 4/1988 | Evans et al. |
| 4,761,471 | A | 8/1988 | Urist |
| 4,774,228 | A | 9/1988 | Seyedin et al. |
| 4,774,322 | A | 9/1988 | Seyedin et al. |
| 4,789,732 | A | 12/1988 | Urist |
| 4,798,885 | A | 1/1989 | Mason et al. |
| 4,804,744 | A | 2/1989 | Sen |
| 4,810,691 | A | 3/1989 | Seyedin et al. |
| 4,843,063 | A | 6/1989 | Seyedin et al. |
| 4,886,747 | A | 12/1989 | Derynck et al. |
| 4,968,590 | A | 11/1990 | Kuberasampath et al. |
| 4,975,527 | A | 12/1990 | Koezuka et al. |
| 5,011,691 | A | 4/1991 | Oppermann et al. |
| 5,106,626 | A | 4/1992 | Parsons et al. |
| 5,108,753 | A | 4/1992 | Kuberasampath et al. |
| 5,187,076 | A | 2/1993 | Wozney et al. |
| 5,393,739 | A | 2/1995 | Bentz et al. |
| 5,631,142 | A | 5/1997 | Wang et al. |
| 5,849,880 | A | 12/1998 | Wozney et al. |
| 6,190,880 | B1 | 2/2001 | Israel et al. |
| 6,207,813 | B1 | 3/2001 | Wozney et al. |
| 6,245,889 | B1 | 6/2001 | Wang et al. |

FOREIGN PATENT DOCUMENTS

| | | |
|---|---|---|
| WO | WO 94/26322 | 11/1994 |

OTHER PUBLICATIONS

Damien et al., "A Composite of Natural Coral, Collagen, Bone Protein and Basic Fibroblast Growth Factor Tested in a Rat Subcutaneous Model", Annales Chirugiae et Gynaecologiae, Supplementum, (1993) 207, 117-38.

Dart et al., Transforming growth factors from a human tumor cell: characterization of transforming growth factor beta and identification of high molecular weight transforming growth factor alpha. Biochemistry, (Oct. 8, 1985) 24 (21) 5925-31.

Gao, T.J., et al., "Microscopic evaluation of bone-implant contact between hydroxyapatite, bioactive glass and tricalcium phosphate implanted in sheep diaphyseal defects," Biomaterials (1995), pp. 1175-1179, vol. 16, Oxford, England.

Gao, T.J., et al., Enhanced Healing of Segmental Tibial Defects in Sheep by a Composite Bone Substitute Comprised of Tricalcium Phosphate Cylinder, Bone Morphogenetic Protein and Type IV Collagen, Journal of Biomedical Materials Research (1996), vol. 32, Interscience, Wiley, Hoboken, NJ.

Gao, T.J., et al., "A coral composite implant containing bone morphogenetic protein repairs a segmental tibial defect in sheep: mechanics and immune assay," International Orthopaedics,, German Ceramics Society, Cologne, Germany.

Gao, T.J., et al., "Comparative Study on Potential of Natural Coral and Tricalcium Phosphate Cylinders in Healing a Segmental Diaphyseal Defect in Sheep," Bioceramics, pp. 199-204, vol. 8, German Ceramics Society, Cologne, Germany.

Gao, T.J., et al., "Composite of Bone Morphogenetic Protein (BMP) and Type IV Collagen, Coral-Derived Coral Hydrozyapatite and Tricalcium Phosphate Ceramics," International Orthopaedics (Accepted), Springer Verlag, Berlin, Germany.

Gao, T.J., et al., "Bone Inductive Potential and Dose-Dependent Response of Bovine Bone Morphogenetic Protein Combined with Type IV Collagen Carrier," Annales Chirurgiae et Gynaecologiae (1993), pp. 77-84, vol. 207, University of Tampere, Finland, University of Helsinki, Finland.

Gao, Tie-Jun, "Bioactive Delivery System for Extracted Bone Morphogenetic Proteins" (1996), Acta Universitatis Tamperensis, ser A, vol. 511, Academic Dissertation, Tampere, Finland.

Harris, E.L.V., "Concentration of the Extract", Chapter 3, In. Protein Purfication Methods: A Practical Approach, Harris et al. (Eds.), Sep. 1989, IRL Press, Oxford, UK, pp. 125-130.

Jortik, Leena, "Native Bone Morphogenetic Protein Purfication and Action On Rat Skeletal Muscle Myoblast" (1998), Academic Dissertation Acta Universitatis Tamperensis 629, Tampere, Finland.

Jortikka, Leena, et al., "Partially Purified Reindeer (*Rangifer tarandus*) Bone Morphogenetic Protein Has a High Bone-Forming Activity Compared With Some Other Artiodactyls," Clinical Orthopaedics and Related Research (1993), pp. 33-37, vol. 297, J. B. Lippincott Company.

Jortikka et al., "Purfication of monocomponent bovine bone morphogenetic protein in a water-soluble form", Annales Chirugiae et Gynacologiae, Supplementum, (1993) 207:25-30.

Kirker-Head, Carl A., et al., "Long-Term Healing of Bone Using Recombinant Human Bone Morphogenetic Protein 2," Clinical Orthopaedics and Related Research (1995), pp. 222-230, vol. 318, Lippincott-Raven Publishers.

Lindholm, T.S. and Gao, T.J., "Functional Carriers for Bone Morphogenetic Proteins," Annales Chirurgiae et Gynaecologiae Supplementum, (1993), pp. 3-12, vol. 82, University of Helsinki, Helsinki, Finland.

Lindholm, Tom C., "Calvarial Reconstruction With Implants Of: Hydroxyapatite, Autogenous Bone Marrow, Allogeneic Demineralized Bone Matrix and Bovine Bone Morphogenetic Protein," Dissertation, University of Tampere and University of Turku, Finland (1995), pp. 8-280, Laatupaino-Yhtiöt Oy, Rauma, Finland.

Lindholm, T. Sam, M.D., Ph.D., "Tissue Engineering Intelligence Unit, Bone Morphogenetic Proteins: Biology, Biochemistry and Reconstructive Surgery" (1996), Chapter 3, 6, 12, 14, 15, 18, 19, R.G. Landes Company and Academic Press, Inc., Georgetown, Texas.

Lindholm, T. S., et al., "Biological Activity of BMP to Type 1 and IV Collagen: A Preliminary Report," Department of Clinical Sciences, University of Tampere, pp. 45-50, Tampere, Finland.

Marttinen, A., et al., "Protein in a Water-Soluble Form," New Trends in Bone Grafting (1991), pp. 40-43, Acta Universitatis Tamperensis, ser B vol. 40, Tampere, Finland.

Ogawa et al., "Bovine bone activin enhances bone morphogenetic protein-induced ectopic bone formation", J. Biol. Chem. (Jul. 15, 1992) 267 (20 ) 14233-7.

Pajamäki, K.J.J., et al., "Bone Matrix in Rat Abdominal Muscle Pouch," University of Tampere, Tampere; Abo Akademi University, Turku, University of Turku, Turku, Finland, pp. 132-138.

Pajamäki, K.J.J., et al., "Fibronectin and Collagen Types I and III in Aggressive Granulomatous Lesions Surrounding Hip Implants," University of Tampere, Tampere, Finland, pp. 300-304.

Sampath, T.K. & Reddi, A.H., "Homology of bone-inductive proteins from human, monkey, bovine, and rat extracellular matrix," Proc. Natl. Acad. Sci. USA (1983), pp. 6591-6595, vol. 80, National Academy of Sciences, Washington, DC.

Sampath, T. Kuber, et al., "Bovine Osteogenic Protein Is Composed of Dimers of OP-1 and BMP-2A, Two Members of the Transforming Growth Factor-β Superfamily," The Journal of Biological Chemistry (1990), pp. 13198-13205, vol. 265, No. 22, The American Society for Biochemistry and Molecular Biology, Inc.

Urist, M. R., et al., "Native Bone Morphogenetic Protein," University of Tampere Editiorial Board (1992), pp. 27-39, Tampere, Finland.

Urist, M. R., et al., "Purfication of bovine bone morphogenetic protein by hydroxyapatite chromatography," *Proc. Natl. Acad. Sci. USA* (1984), pp. 371-375, vol. 81.

Urist, Marshall R., "The search for and the discovery of bone morphogenetic protein (BMP)," Bone Grafts, Derivatives and Substitutes (1994), Chapter 17, pp. 315-362, Butterworth-Heinemann Ltd., Jordan Hill, Oxford, U.K.

Viljanen, V.V., et al., "Partial Purfication and Characterization of Bone Morphogenetic Protein from Bone Matrix of the Premature Moose (*Alces alces*): Degradation of Bone-Inducing Activity during Storage," (1996), pp. 447-460, vol. 28, European Surgical Research, Karger, Basel, Switzerland.

Viljanen, V. V., et al., "Xenogeneic moose (*Alces alces*) bone morphogenetic protein (mBMP)-induced repair of critical-size skull defects in sheep," International Journal of Oral Maxillofacial Surgery (1996), pp. 217-222, vol. 25, University of Tampere, Tampere and University of Helsinki, Helsinki, Finland.

Viljanen, V. V., et al., "List of References On Demineralized Bone Matrix Induced Osteogenesis and Research of Bone Morphogenetic Proteins During the Period From 1951 Through 1995," Tissue Engineering Intelligence Unit, Bone Morphogenetic Proteins: Biology, Biochemistry and Reconstructive Surgery (1996), Appendix pp. 242-308, R. G. Land.

Aaboe, M., et al., "Healing of experimentally created defects: a review," British Journal of Oral & Maxillofacial Surgery (1995), pp. 312-318, vol. 33, Churchill Livingstone, Edinburgh, Scotland.

Boden, S.D. et al., "Video-Assisted Lateral Intertransverse Process Arthrodesis," Spine (1996), pp. 2689-2697, vol. 21, Lippincott Williams & Wilkins, Hagerstown, MD.

Bostrom, M., et al., "Use of Bone Morphogenetic Protein-2 in the Rabbit Ulnar Nonunion Model," Clinical Orthopaedics and Related Research (1996), pp. 272-282, No. 327, Lippincott Williams & Wilkins, Philadelphia, PA.

Clement, J.H., et al. "Bone morphogenetic protein 2 in early development of *Xenopus laevis*, " Mechanisms of Development (1995), pp. 357-370, vol. 52, Elsevier Science, Limerick, Ireland.

Cook, S.D., et al., "Recombinant Human Bone Morphogenetic Protein-7 induces Healing in a Canine Long-Bone Segmental Defect Model," Clinical Orthopaedics and Related Research (1994), pp. 302-312, No. 301, J.B. Lippincott, Philadelphia, PA.

Cook, S.D., et al., "The Effect of Recombinant Human Osteogenic Protein-1 on Healing of Large Segmental Bone Defects," The Journal of Bone and Joint Surgery, (1994), pp. 827-838, vol. 76-A, Amer. Vol., Boston, MA.

Cook, S.D., et al., "*In Vivo* Evaluation of Recombinant Human Osteogenic Protein (rhOP-1) Implants As a Bone Graft Substitute for Spinal Fusions," Spine (1994), pp. 1655-1663, vol. 19, Lippincott Williams & Wilkins, Hagerstown, MD.

Cook, S.D., et al., "Effect of Recombinant Human Osteogenics Protein-1 on Healing of Segmental Defect in Non-Human Primates," BOSTON Journal of Bone and Joint Surgery, (1995), pp. 734-750, American ed. 77(5), Boston, MA.

Cook, S.D., et al., "Osteogenic Protein-1," Clinical Orthopaedics and Related Research (1996), pp. 29-38, No. 324, JB Lippincott, Philadelphia, PA.

Dudley, A.T., et al., "A requirement for bone morphogenetic protein-7 during development of the mammalian kidney and eye," Genes & Development (1995), pp. 2795-2807, vol. 9, Cold Spring Harbor Laboratory Press, Cold Spring Harbor, NY.

Ehrnberg, A., et al., "Comparison of Demineralized Allogeneic Bone Matrix Grafting (the Urist Procedure) and the lizarov Procedure in Large Diaphyseal Defects in Sheep," The Journal of Bone and Joint Surgery, (1993), pp. 438-447. vol. 11, Orhtopaedic Research Society, American Ed. Journal of Bone and Joint Surgery, Boston, MA.

Einhorn, T.A., et al., "The Healing of Segmental Bone Defects Induced by Demineralized Bone Matrix," The Journal of Bone and Joint Surgery (1984), pp. 274-279, vol. 66-A, The Journal of Bone and Joint Surgery, Boston, MA.

Fang, J., et al., "Stimulation of new bone formation by direct transfer of osteogenic plasmid genes," Proc. Natl. Acad. Sci. (1996), pp. 5753-5758, vol. 93 (USA), National Academy of Sciences, Washington, DC.

Fischgrund, J.S., et al., "Augmentation of Autograft Using rhBMP-2 and Different Carrier Media in the Canine Spinal Fusion Model", Journal of Spinal Disorders (1996), pp. 467-472, vol. 10, No. 6, Lippincott Williams & Wilkins, Hagerstown, MD.

Gerhart, T.N., et al., "Healing Segmental Femoral Defects in Sheep Using Recombinant Human Bone Morphogenetic Protein," Clinical Orthopaedics and Related Research (1993), pp. 317-326, No. 293, J.B. Lippincott Company, Philiadelphia, PA.

Heckman, J.D., et al., "The Use of Bone Morphogenetic Protein in the Treatment of Non-Union in a Canine Model," The Journal of Bone and Joint Surgery (1991), pp. 750-764, vol. 73-A, The Journal of Bone and Joint Surgery, American Volume, Boston, MA.

Helm, G.A., et al., "Utilization of type 1 collagen gel, demineralized bone matrix, and bone morphogenetic protein-2 to enhance autologous one lumbar spinal fusion," J. Neurosurgery. (1997), pp. 93-100, vol. 86, Charlottesville, VA.

Hogan, B.L.M., "Bone morphogenetic proteins: multifunctional regulators or vertebrate development," Genes & Development (1996), pp. 1580-1594, vol. 10, Cold Spring Harbor Laboratory Press, Cold Spring Harbor, NY.

Holliger, E.H., et al., "Morphology of the Lumbar Intertransverse Process Fusion Mass in the Rabbit Model: A Comparison Between Two Bone Graft Materials–rhBMP-2 and Autograft," Journal of Spinal Disorders (1996), pp. 125-128, vol. 9, Lippincott Williams & Wilkins, Hagerstown, MD.

Hollinger, J. & Leong, K., "Poly($\alpha$-hydroxy acids): carriers for bone morphogenetic proteins," Biomaterials (1996), pp. 187-194, vol. 17, Elsevier Science Limited, Butterworth-Heinemann, Oxford, England.

Hotz, G. & Harr, G., "Bone substitute with osteoinductive biomaterials - current and future clinical applications," Int. J. Oral Maxillofac. Surg. (1994), pp. 413-417, vol. 23, Munksgaard, Copenhagen, Denmark.

Hu, Y.Y., "Experimental studies on reconstituted xenograft and its clinical application," Chinese Journal of Surgery, vol. 31, No. 12, pp. 709-713, Zhonghua yi xue hui, Wai ke xue hui, Beijing, China.

Johnson, E.E. & Urist, M.R., "Distal Metaphyseal Tibial Nonunions Associated with Significant Bowing Deformity and Cortical Bone Loss: Treatment with Human Bone Morphogenetic Protein (h-BMP) and Internal Fixation," (1989), pp. 613-620, vol. 63, Nippon Seikeigeka Gakkai Zasshi, Japan.

Johnson, E.E., et al., "Repair of Segmental Defects of the Tibia with Cancellous Bone Grafts Augmented with Human Bone Morphogenetic Protein," Clinical Orthopaedics and Related Research (1988), pp. 249-257, No. 236, JB Lippincott, Philiadelphia, PA.

Johnson, E.E., et al., "Bone Morphogenetic Protein Augmentation Grafting of Resistant Femoral Nonunions," Clinical Orthopaedics and Related Research (1988), pp. 257-265, No. 230, JB Lippincott, Philadelphia, PA.

Johnson, E.E., et al., "Autogeneic Cancellous Bone Grafts in Extensive Segmental Ulnar Defects in Dogs," Clinical Orthopaedics and Related Research (1989), pp. 254-265, No. 243, JB Lippincott, Philadelphia, PA.

Kato, F., "Experimental study of chemical spinal fusion in the rabbit by means of bone morphogenetic protein," (1990), PubMed 2380596, Nippon Seikeigeka Gakkai Zasshi, Japan.

Kuboki, Y., et al., "Two Distinctive BMP-Carriers Induce Zonal Chondrogenesis and Membranous Ossification, Respectively: Geometrical Factors of Matrices for Cell-Differentiation," Connective Tissue Research (1995), pp. 219-226, vol. 32, Taylor & Francis, Philiadelphia, PA.

Lee, S.C., et al., "Healing of large segmental defects in rat femurs is aided by RhBMP-2 in PLGA matrix," Journal of Biomedical Materials Research (1994), pp. 1149-1156, vol. 28, Wiley Interscience, Hoboken, NJ.

Linde, A. and Hedner, E., "Recombinant Bone Morphogenetic Protein-2 Enhances Bone Healing, Guided by Osteopromotive e-PTFE Membranes: An Experimental Study in Rats," Calcified Tissue Int. (1995), pp. 549-553, vol. 56, Springer-Verlag, NY.

Lindholm, T.S., et al., "Response of Bone Marrow Stroma Cells to Demineralized Cortical Bone Matrix in Experimental Spinal Fusion in Rabbits," Clinical Orthopaedics and Related Research (1988), pp. 296-302, No. 230, JB Lippincott, Philiadelphia, PA.

Lindholm, T.C., et al., "Bone Morphogenetic Proteins Regenerating Skull and Maxillo-Mandibular Defects," Bone Morphogenetic Proteins (1996), pp. 149-155, R.G. Landes Company, Austin, TX.

Lovell, T. P., et al., "Augmentation of Spinal Fusion With Bone Morphogenetic Protein in Dogs," Clinical Orthopaedics And Related Research (1989), pp. 266-274, No. 243, JB Lippincott, Philadelphia, PA.

Miyamoto, S. & Takaoka, K., "Bone Induction and Bone Repair by Composites of Bone Morphogenetic Protein and Biodegradable Synthetic Polymers," Annales Chirurgiae Et Gynaecologiae Supplement. 69-76, vol. 82, University of Helsinki, Helsinki, Finland.

Muschler, G.F., et al., "Evaluation of Human Bone Morphogenetic Protein 2 in a Canine Spinal Fusion Model," Clinical Orthopaedics And Related Research (1994), pp. 229-240, No. 308, J.B. Lippincott Company, Philadelphia, PA.

Nilsson, O.S., et al., "Bone Repair Induced by Bone Morphogenetic Protein in Ulnar Defects in Dogs," The Journal Of Bone And Joint Surgery, British Volume, (1986), pp. 635-642, vol. 68-B, London, UK.

Oda, S., et al., "Ectopic bone induction in recombinant human bone morphogenetic protein-2 (rhBMP-2) combined with biphasic calcium phosphate (BCP)," (1996), The Journal of Stomatological Society, Japan.

Ono, I., et al., "Promotion of the Osteogenetic Activity of Recombinant Human Bone Morphogenetic Protein by Prostaglandin $E^1$," Bone (1996), pp. 581-588, vol. 19, Elsevier Science Inc., NY.

Panganiban, G.E.F., et al., "Biochemical Characterzation of the *Drosophila dpp* Protein, a Member of the Transforming Growth Factor β Family of Growth Factors," Molecular and Cellular Biology (1990), pp. 2669-2677, vol. 10, American Society for Microbilogy, Washington, DC.

Petit, J.C. & Ripamonti, U., "Tissue Segregation Enhances Calvarial Osteogenesis in Adult Primates," The Journal of Craniofacial Surgery (1994), pp. 34-43, vol. 5, Little, Brown & Co., Boston, MA.

Ragni, P. & Lindholm T.S., "Interaction of Allogeneic Demineralized Bone Matrix and Porous Hydroxyapatite Bioceramics in Lumbar Interbody Fusion in Rabbits," Clinical Orthopaedics and Related Research (1991), pp. 292-299, No. 272, JB Lippincott, Philadelphia, PA.

Ragni, P., et al., "Spinal Fusion Induced by Porous Hydroxyapatite Blocks (HA)," pp. 133-144, Italian Journal of Orthopaedics & Traumatology, Bologna, Italy.

Ragni, P.C. & Lindholm, T.S., "Bone Formation and Static Changes in the Thoracic Spine at Uni- or Bilateral Experimental Spondylodesis with Demineralized Bone Matrix (DBM)," pp. 237-252, Italian Journal of Orthopaedics & Traumatology, Bologna, Italy.

Riley, E.H., et al., "Bone Morphogenetic Protein-2," Clinical Orthopaedics and Related Research (1996), pp. 39-46, No. 324, JB Lippincott, Philadelphia, PA.

Sailer, H.F. & Kolb, E., "Application of purified bone morphogenetic protein (BMP) preparations in cranio-maxillo-facial surgery," Journal of Cranio-Maxillo-Facial Surgery (1994), pp. 191-199, vol. 22, Churchill Livingstone, Edinburgh, Scotland.

Sailer, H.F. & Kolb, E., "Application of purified bone morphogenetic protein (BMP) in cranio-maxillo-facial surgery," Journal of Cranio-Maxillo-Facial Surgery (1994), pp. 2-11, vol. 22, Churchill Livingstone, Edinburgh, Scotland.

Sampath, T.K., et al., "*Drosophila* transforming growth factor β superfamily proteins induce endochondral bone formation in mammals," Proc. Natl. Acad. Sci. USA (1993), pp. 6004-6008, vol. 90, National Academy of Sciences, Washington, DC.

Sandhu, H.S., et al., "Evaluation of rhBMP-2 With an OPLA Carrier in a Canine Posterolateral (Transvers Process) Spinal Fusion Model," SPINE (1995), pp. 2669-2683, vol. 20, Lippincott-Raven Publishers.

Sandhu, H.S., et al., "Effective Doses of Recombinant Human Bone Morphogenetic Protein-2 in Experimental Spinal Fusion," SPINE (1996), pp. 2115-2122, vol. 21, Lippincott Williams & Wilkins, Hagerstown, MD.

Schimandle, J.H., et al., "Experimental Spinal Fusion With Recombinant Human Bone Morphogenetic Protein-2," SPINE (1995), pp. 1326-1337, vol. 20, Lippincott Williams & Wilkins, Hagerstown, MD.

Sheehan, J.P., et al., "Molecular Methods of Enhancing Lumbar Spine Fusion," Neurosurgery (1996), pp. 548-554, vol. 39.

Staehling-Hampton, K., et al., "Specificity of Bone Morphogenetic Protein-related Factors: Cell Fate and Gene Expression Changes in *Drosophila* Embryos induced by *decapentaplegic* but not 60A," Cell Growth & Differentiation (1994), pp. 585-593, vol. 5, American Association for Cancer Research, Philadelphia, PA.

Sun, Y., et al., "Repair of large cranial defect using allogeneic cranial bone and bone morphogenetic protein," PubMed 7600438 (1995), Chinese Journal of Plastic Surgery and Burns, Beijing, China.

Toriumi, D.M., et al., "Mandibular Reconstruction With a Recombinant Bone-Inducing Factor," Arch Otolaryngol Head Neck Surg (1991), pp. 1101-1112, vol. 117, American Medical Association, Chicago, IL.

Urist, M.R., et al., "Regeneration of an enchondroma defect under the influence of an implant of human bone morphogenetic protein," The Journal of Hand Surgery (1986), pp. 417-419, vol. 11A, Churchill Livingstone, Secaucus, NJ.

Van Eeden, S.P. & Ripamonti, U., "Bone Differentiation in Porous Hydroxyapatite in Baboons is Regulated by the Geometry of the Substratum: Implications for Reconstructive Craniofacial Surgery," Plastic and Reconstructive Surgery (1994), pp. 959-966, vol. 93, Lippincott Williams & Wilkins, Hagerstown, MD.

Viljanen, V.V., "Allogeneic and xenogeneic bone morphogenetic protein in skeletal reconstruction," (Academic Dissertation) University of Tampere (1997), Tampere, Finland.

Wharton, K.A., et al., "*Drosophila* 60A gene, another transforming growth factor β family member, is closely related to human bone morphogenetic proteins," Proc. Natl. Acad. Sci. USA (1991), pp. 9214-9218, vol. 88, National Academy of Sciences, Washington, DC.

Wolfe M.W. & Cook, S.D., "Use of osteoinductive implants in the treatment of bone defects," Medical Progress Through Technology (1994), pp. 155-168, vol. 20, Kluwer Academic, Boston, MA.

Yasko, A.W., et al., "The Healing of Segmental Bone Defects, Induced by Recombinant Human Bone Morphogenetic Protein (rhBMP-2)," The Journal Bone and Joint Surgery, (1992), pp. 639-670, vol. 74-A, American Ed. Journal of Bone and Joint Surgery, Boston, MA.

OSTEOGENIC DEVICE AND A METHOD FOR PREPARING THE DEVICE

CROSS-REFERENCE TO RELATED APPLICATIONS

This application is a divisional of Application No. 09/125,963, filed on Nov. 24, 1998, now abandoned which was a national stage filing under 35 U.S.C. § 371 of International Application No. PCT/FI96/00118 filed on Feb. 29, 1996.

THE TECHNICAL FIELD

The present invention is related to an osteogenic device and a method for preparing said device, which has improved osteoinductive properties. The invention also relates to the use of a specific bone morphogenetic protein complex in the preparation of an osteogenic device with improved properties.

THE BACKGROUND OF THE INVENTION

It is a great challenge in the orthopedic and periodontal surgical fields to find systems for treating patients with skeletal disorders and deformations, including the repairing of large bone defects originating from trauma, excision of tumours and congenital malformations, reconstructing bone stocks worn off by an implanted endoprothesis in revision operations and healing delayed or non-united fractures.

Autogeneic cancellous bone grafts harvested from human bone have been the most reliable and effective alternative to bone substitute so far. However, restricted availability of sources, suffering caused by explanting surgery and the risk of transmission of human immunodeficiency virus and of other complications limit its extensive clinical use. Raised incidences of stress fracture, nonunion and failure of incorporation of cancellous bone grafts have also been reported as the defect sizes extends. The synthesized biomaterials which have been commercialized can only be used as filling material or supporting scaffold without biological activity in initiating bone regeneration. A desirable bone substitute such as investigators and clinicians have sought might be a reconstitution of synthetic material possessing chemical composition, geometrical architecture, mechanical integrity and biocompatibility similar to those of the bulk of living bone, with biological growth factors able to induce or improve bone regeneration. Such a substitute can hopefully replace autografts and be extensively applied in all contexts related to hard tissue transplantation in clinical medicine. Commercially available synthesized biomaterials have been developed and can be used as filling material or inlay as well as onlay support. Unfortunately, these materials lack the biological activity in initiating bone regeneration. Synthetic carriers prepared from such materials as polylactic acids and hyaluronic acids are described e.g. in the patent U.S. Pat. No. 5,366,508. Bone morphogenetic protein (BMP) is an important factor in osteogenic devices and participates actively in the implantation process.

BMP has been the target for a tremendous amount of research, since the significance of BMP in skeletal biology was first recognized and the methods for its extraction and purification were published by Urist—one of the pioneers in the field of BMP research. BMP has also occasionally been used for treating patients with delayed union of fractures, but it has not yet been used in great scale for treating patients. Important milestones in the history of BMP are the discovery of the effectiveness of BMP in induction of new bone formation, the development of isolation methods for partially purified naturally occurring BMP from animal bone matrix and the isolation of different cDNAs encoding BMPs, which enables the preparation of BMP with recombinant DNA techniques.

The development of recombinant DNA techniques makes it possible to produce recombinant human bone morphogenetic proteins (rhBMPs). However, the rhBMPs have not yet been approved for use in clinical treatments. Preliminary experiments have indicated that rhBMP has a biological activity and probably may have some immunological advantages compared with native BMPs. However, the biological activity of rhBMP is only one tenth or less of the biological activity of purified or partially purified native BMP (Bessho, K., et al., Personal Communications; Protein, (In press) 1966).

The preliminary results have led to the development of a multitude of biological delivery systems for BMP in vivo. Even if the experiments with highly purified naturally occurring BMP or recombinant BMP given without carriers have given positive results, the BMP without a carrier rapidly dissolves and diffuses in the body fluids after implantation and soon thereafter expression of osteoinductivity is impeded. Thus, an appropriate functional carrier of BMP is needed to potentate and modulate the activity of BMP. However, so far the results with BMP isolated with conventional methods or rBMP combined with conventional carriers have not been as encouraging as expected.

The carrier or delivery system of the osteoinductive BMP in implants has a great effect on the biological activity of BMP. The carrier protects BMP from rapid outward diffusion and endogenous proteinization. It retains a persistent concentration gradient of BMP coinciding with differentiation of BMP target cells and osteogenesis. Further, it provides a scaffold for attachment of BMP responsive cells.

Delivery systems for BMP has not only been discussed in a multitude of publication, they have also been extensively disclosed in several patents and patent applications. For example, the patent U.S. Pat. No. 5,443,531 discloses a delivery system in which BMP is adsorbed on a hydroxyapatite carrier in a chromatography column.

In order to improve the properties of the delivery systems for administering BMP in clinical applications, collagens, especially type IV collagen, have been used to impregnate carriers and improve biological activity. In the patents U.S. Pat. No. 4,975,527 and U.S. Pat. No. 4,394,370 collagen based carriers for BMP are disclosed. The bone inductive potential and dose-dependent response of bovine BMP combined with a type IV collagen carrier is discussed in Gao et al., Ann. Chir. Gynec. 82: 77–84, 1993.

A desirable bone substitute would be a material lacking the risks related to human derived autografts, possessing the properties of a synthetic material, i. e. having a chemical composition and a geometrical architecture and a mechanical integrity and strength similar to the bulk of living bone autografts and at the same time having the biological activity including growth factors, which are able to induce or improve bone regeneration.

Gao et al., (Biomaterials 16, 1175–1179, 1995) have published an article about the microscopic evaluation of bone implant contact between hydroxyapatite, bioactive glass and tricalcium phosphate implanted in sheep diaphyseal defects.

Promising results have been obtained with so called bioceramics, such as biocorals originating from the skeleton of corals. Biocoral have been extensively used as carriers. The use of calcium carbonate originating from coral skeleton as bioresorbable bone material has been described e.g. in the patent U.S. Pat. No. 5,433,751 and the patent publication WO 93/02181.

The use of the biocoral carriers in combination with certain growth factors, such as TGF, has been disclosed in the patent publication WO 94/26322. The use of the growth factor TGF in combination with BMP is also disclosed in the patent U.S. Pat. No. 5,393,739.

Even if a multitude of different delivery systems for BMP have been suggested and different systems have been experimentally tested (Lindholm & Gao, Ann. Chir. Gynaecol. 82, 3–12, 1993) no fully satisfying combination of BMP and carrier has so far been discovered for clinical treatment of human patients.

It has also been shown that BMPs isolated by the conventional methods in addition to decreased induction of bone formation cause immunogenic and inflammatory reactions.

Thus, there is a great need to develop novel alternative, osteogenic devices for improved delivery of BMP to obtain an improved osteoinductive effect. At the same time it is important to obtain an osteogenic device with decreased immunogenic properties.

The main objective of the present invention is to provide an osteogenic device which has improved inductive activity in bone formation and with less immunogenic and inflammatory reactions, which device is useful in ectopic bone induction and healing of segmental bone defects in vertebrates.

Another objective of the present invention is to provide a novel osteogenic device with improved osteoinductive properties for improved bioactive delivery of BMP, especially modified BMP.

A further objective of the present invention is to improve the bioactive delivery system for BMP by increasing the biological potential of the delivery system by impregnating the carrier, especially a bioceramic carrier with collagen.

The objective of the present invention is to provide a new osteogenic device with improved resorbability.

It is further an objective to provide a modified BMP complex with improved storability.

THE SUMMARY OF THE INVENTION

The characteristics of the improved osteogenic device, which solves the problems set forth above is defined in the claims as well as the characteristics of the method of preparing said osteogenic device.

The present invention is related to an osteogenic device, which comprises at least one type of bone morphogenetic protein (BMP), preferably a modified BMP complex, which is essentially free from a 25–55 kD protein with immunogenic and inflammatory properties, a suitable combination of collagens, preferably a collagen mixture, Type I collagen or Type IV collagen and a suitable carrier, preferably a shapable body, block or cylinder consisting of hydroxyapatite, tricalcium phosphates or bioceramics or most preferably biocoral originating from natural coral skeleton, but also combination of all types of carriers mentioned are possible.

The osteogenic device can optionally include growth factors, such as TGF.

The bone morphogenetic protein can be a BMP purified by conventional methods or a BMP produced by recombinant DNA techniques. Preferably the BMP should be isolated with the method developed by the inventors of the present patent application and described below, which method is a modification of the methods developed by Urist and described e.g. in Urist et al.; In Lindholm TS (ed): New Trends in Bone Grafting. Acta Universitatis Tamperiensis, University of Tampere, 1992, ser. B vol. 40, pp. 27–39. It is appreciated by those skilled in the art that BMP corresponding to said modified BMP complex and its osteoinductive components can be prepared by recombinant DNA techniques in the future.

The preferred modified BMP complex comprises a mixture of a high molecular weight (MW) BMP fraction and a low MW kD protein fraction and is further characterized by being a non-gelatinized, non-collagenic, lipid-containing osteo-inductive polypeptide BMP, from which an immunogenic, inflammation causing fraction has been removed.

The preferred modified BMP complex (mBMPc) is obtainable by a method comprising the steps of:

(a) extracting the pulverized or ground bone material with guanidinium hydrochloride (GuHCl). Preferably a 1.5–5.0 M solution, most preferably a 4 M solution is used;

(b) performing a HPCL gel filtration to obtain a high, medium and low MW protein fraction from the extract obtained in step (a). Said three fractions are characterized by having different molecular weights, Fraction I is a high MW (100–700 kD) protein with osteoinductive BMP activity, Fraction II is a medium MW (25–55 kD) immunogenic protein lacking BMP activity and Fraction III is a low MW (15–25 kD) protein with osteoinductive BMP activity; and (c) drying and sterilizing Fraction III, the low MW osteoinductive BMP fraction with improved storability.

In another preferred embodiment of the invention a suitable mBMPc is obtainable by steps (a) and (b) followed by the following steps:

(c) combining the high and low MW fractions Fractions I and III obtained in step (b) to obtain a mixture of said fractions; and (d) drying and sterilizing the mixture obtained in step (c) for prolonged storage.

Alternatively, the mBMPc is obtainable by using a method in which further to the above-defined steps the following optional steps are included:

(1) performing at least one dialysis against water or a suitable buffer solution of the extract obtained in step (a), preferably two dialysis steps one against water and one against a suitable buffer solution;

(2) performing at least one hydrolysis step with collagenase;

(3) filtering the extract from steps a and/or b and/or c by a tangential flow system and/or a ultrafiltration system to obtain a concentrated solution; and (4) purifying the BMP extract with any useful protein purification method, which does not essentially disturb, the properties obtainable by the steps listed above.

The invention is also related to a method for preparing the osteogenic device described above.

Collagens, preferably collagen I, collagen IV or commercially available collagen mixtures are incubated with dissolved partially purified or purified native or recombinant BMP or a modified BMP complex. The preferred BMP is obtainable by a method modified from the method described by Urist et al.; In Lindholm TS (ed): New Trends in Bone Grafting. Acta Universitatis Tamperiensis, University of Tampere, 1992, ser. B vol. 40, pp. 27–39. The mBMPc of the present invention is characterized by comprising a mixture of a high MW protein and a low MW protein fraction with BMP activity and lacking essentially a medium MW immunogenic protein.

The carrier, preferably the bioceramic carrier body, most preferably the biocoral derived from a coral skeleton is immersed in the BMP-collagen solution and incubated for a time sufficient for the BMP to impregnate the collagen. The BMP-collagen-bioceramic body is dialysed and the body and the solution used for dialysis are separated. Any precipitated remnants, residues or rests of BMP from the solution used for dialysis is adsorbed on the shapable porous carrier, to give a bioceramical, osteogenic device. Said device is dried and sterilized with approved conventional methods for prolonged storage.

A BRIEF DESCRIPTION OF THE DRAWINGS

FIG. 1 depicts a Sephacryl$^R$ S-200 gel-filtration chromatogram of semipurified moose BMP. The fractions collected for further analysis are shown. Fractions I and III showed osteoinductivity in a mouse bioassay. Specifications: flow rate 0.9 ml/min. Running buffer: 0.06 M K-phosphate, Ph 6.9+150 mM naCl+6M urea+detergents. Injection volume 1.8 ml. Injection quantity 120 mg.

Figure 2:
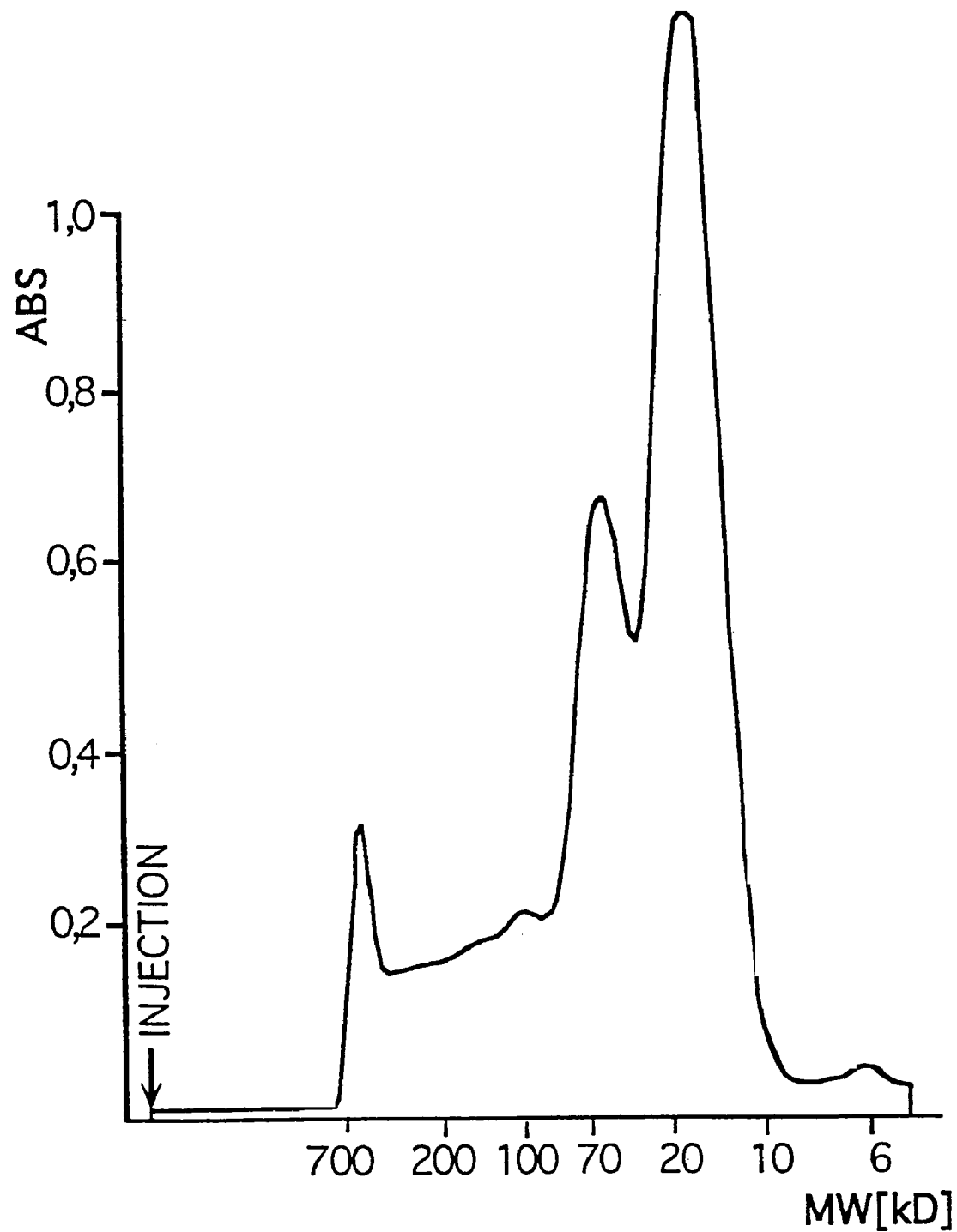

FIG. 2. shows a HPLC chromatography defining partially purified moose BMP preparation as a multimer composed of three major fractions with the molecular weight ranged from 11–40, 40–140 and 500–700 KD respectively.

Figure 3:
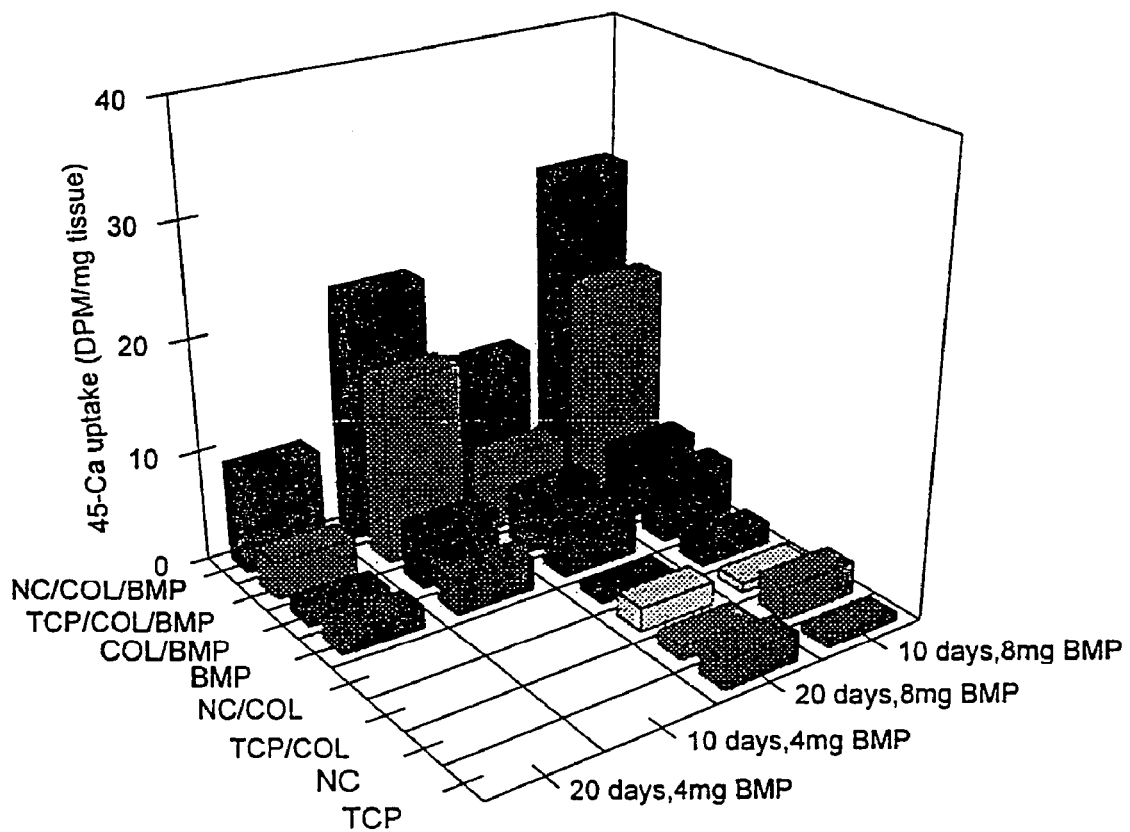

FIG. 3. shows the variations of $^{45}$Calcium incorporation in the different kind of implants in the muscle pouches of BALB mice at the 10th and 20th day after implantation. The osteogenic devices used are marked as follows: natural coral-collagen-BMP (NC/COL/BMP), tricalcium phosphate-collagen-BMP (TCP/COL/BMP), collagen-BMP (COL-BMP), bone morphogenetic protein as such (BMP), natural coral-collagen (NC/COL), tricalcium phosphate-collagen(TCP-COL), natural coral (NC), tricalcium phosphate (TCP).

THE DETAILED DESCRIPTION OF THE INVENTION

Definitions

In the present invention several terms are used as set forth in the field of bone grafting, but some terms are extensively used in a somewhat modified meaning. Therefore, the terms used in the specification and claims are defined in more detail below.

The term osteogenic device means a delivery system for osteoinductive BMP, which includes collagen impregnated on composite material which consists of at least one shapable, porous carrier, preferably a bioactive carrier, including biocorals, hydroxyapatite, bioactive glass, or other acceptable materials conventionally used in bone surgery.

The term osteoinductive means a process whereby one tissue or products derived from it, causes a second undifferentiated tissue to differentiate into bone tissue. The process is involved in the interaction between two systems, the inducing and reacting system. The inducing system in osteoinduction includes hypertrophied cartilage, newly formed or demineralized bone matrix, transitional epithelium and BMP. The reacting target consists of mesenchymal tissue cells having the competence to become osteoblasts.

With the term osteoconduction is meant that implanted material serves as a relatively inert trellis for creeping substitution of host bone.

The term osteogenesis means a process of new bone formation by surviving pre-osteoblasts and osteoblasts within autografts or around injured bone tissue in situ.

The term bone morphogenetic protein (BMP) means the partially or fully purified native BMP obtainable from natural bone sources by previously known, frequently used isolating methods.

Bone morphogenetic protein (BMP) is a non-specific, hydrophobic matrix glycoprotein, which belongs to the family of β-transforming growth factors (TGF-β). Being a differentiation factor and a mitogen, BMP plays an important role in both the chondrogenesis and osteogenesis of embryonic as well as postfetal life. Natural BMP has been extracted and characterized from bovine, human, porcine, rabbit, rat, osteosarcoma tissue as well as moose and reindeer. Differences in recovery amount in the process of extraction and in osteoinductive efficacy in biological assay have shown that BMP has species discrepancies among these different origins. However, for human treatment only specific, approved types of BMP can be used.

The term recombinant bone morphogenetic protein (rBMP), especially the rBMP of human origin (rhBMP) is a BMP obtainable by conventional recombinant DNA techniques.

The term modified bone morphogenetic protein complex (mBMPc) means a bone morphogenetic protein which comprises a mixture of a high MW (100–700 kD) BMP fraction and a low MW (15–25 kD) BMP fraction, which complex is essentially free from a immunogenic and inflammatory protein fraction with a MW of 25–55 kD. Said mBMPc is obtainable by a method comprising at least the steps of extracting ground, demineralisized bone with GuHCl and fractionation with HPCL gel fractionation defined in the claims.

In the present invention the term collagen means primarily Type I collagen, which is the main collagen in bone matrix or Type IV collagen which is the major component of basement membranes, which are involved in cell differentiation and orientation, membrane polarization, selective permeability to macromolecules and migration of various cell types, but also other types of collagens, especially atelopeptide collagens and their mixtures including commercially available collagen mixtures are included in this definition.

The term ceramics preferably means bioceramic carriers, which consist of shapable bodies, blocks or cylinders, such as hydroxyapatite, tricalcium phosphate, bioactive glass and especially biocoral originating from natural coral skeletons.

Coral is the limestone skeleton of various species of marine invertebrates. Porous structure and dimensions in certain types of coral microscopically resemble human trabecular bone.

The dominant inorganic components of coral in the form of aragonite crystal consists mainly of calcium carbonate (98% $CaCO_3$) but also minor amounts of fluoride, strontium and magnesium.

Since implantable BMP spreads rapidly in vivo, one of the most challenging ramifications of BMP research is screening for an ideal delivery system that allows BMP to be effective in small amounts for a prolonged time before BMP can be introduced from basic science laboratory to clinical application.

Noncollagenous protein, collagens, hydroxyapatite, tricalcium phosphate, polylactic acid and titanum have been probed as conveyers of BMP (Lindholm & Gao, Ann. Chir. Gyn. 82, 3–12, 1993).

The bone inductive potential of collagen Type IV as a carrier of bovine BMP has been defined in previous studies (Lindholm et al., In Lindholm TS (ed): New Trends in Bone Grafting. Acta Universitatis Tamperiensis, University of Tampere, 1992, ser. B vol. 40, pp. 45–50 and Gao et al., Ann. Chir. Gyn. 82, 77–84, 1993). Even if positive results were obtained, the absence of geometry and mechanical integrity will hinder the collagen carrier from being an acceptable bone substitute with both the osteoinduction and osteoconduction expected of a bioactive composite bone substitute. To fulfil the ideal properties of a bone substitute, based on synthetic or natural materials, one of the ideas of the present invention is to use some geometric bioceramics as the skeleton of the BMP carrier. Tricalcium phosphate, composed of the same ions as those constituting the bulk of bone, is widely applied as implantable and coating material in medical practice.

Natural coral and derivatives obtained from mineral skeletons of corals are also used as resorbable, osteoconductive, osteophilic replacements of bone grafts in periodontology. In the present invention experiments have been designed to use Type IV collagen-impregnated natural coral and tricalcium phosphate ceramics as a composite vehicle for BMP. Since there are no reports related to a quantitatively comparative study on the effects of composite carriers on BMP bioactivity in vivo, this study aimed to establish whether the composite carrier is superior to the collagen carrier and which of the composites, natural coral- or tricalcium phosphate-dominated, works better for osteoinduction from the point of view of calcium metabolism.

By combining purified bovine osteoinductive polypeptides such as bovine bone morphogenetic proteins with different carrier materials, an osteogenic device for clinical use was produced. Indications for the use of the osteogenic device were surgical treatment of pseudoarthrosis, non-unions, bone defects, bone cysts or speeding up the repair process of fractures in endoprosthetic surgery.

The minimal dosage of BMP required to induce visible bone formation in vivo was used in practice to evaluate the bioactivity of BMP from different origins. Typically, more than 2 mg of partially purified bovine BMP is needed for intramuscular osteoinduction. The moose BMP for example was imbued with a high osteoinductive potential, since radiologically detectable ectopic osteogenesis was observed with as low as 0.2–2.0 mg of partially purified moose BMP. Compared with bovine BMP, a relatively high recovery of moose BMP in the process of extraction showed that BMP content was abundant in diaphyseal bone of the wild premature moose. Although it has been established that the amount of BMP in young species is richer than in older, variations in BMP quantity and in the expression of phenotypes between wild and domestic animals are still unknown. Being a bioactive entity, undissociated moose BMP is composed of polypeptide fractions that cover a wider range of molecular weights. Charged with dominating molecular weights of 11–40 kD, moose BMP combined with aggregates of nonosteogenic matrix proteins that mediate the osteoinductive activity of moose BMP to the target cells might explain why partially purified moose BMP possesses a strong potential for bone induction. High osteoinductivity, rich content and large molecular multimer of bioactive form were the ostensible characteristics of moose BMP in our preliminary identification.

Calcium deposition at the implanted site indicates metabolically osteogenesis in the early stage. The peak of calcium precipitation in newly formed bone usually takes place between 10–20 days in rodents. Significantly increased $^{45}$calcium incorporation in the sites implanted with the composite preparations indicated quantitatively that composite carriers, natural coral or tricalcium phosphate combined with Type IV collagen, functioned much better for delivery of BMP bioactivity than single component carriers. Natural coral and tricalcium phosphate are both calcium-dominated bioceramics with multiporous structure and histocompatibility. Using tricalcium phosphate or Type IV collagen alone as BMP carrier, a favourable result was obtained. It is believed that the porous structure of the ceramics entraps BMP, protects BMP from outward diffusion in vivo and expands the area of reactive cell-BMP contact.

It has been shown that Type IV collagen binds both natural or denaturated BMP and potentiates the effect of BMP on the differentiation and proliferation of mesenchymal cells and osteoprogenitors in vitro. Type IV collagen also avidly binds growth and differentiative factors released from BMP and orient them in an optimal conformation to incite new bone formation locally. The multiporous structure of the ceramics combined with biological modulation of Type IV collagen to BMP bioactivity in the composite preparations considerably augmented the local effect of BMP on inducable cells to improve osteogenesis. The ceramic skeleton in a composite carrier thus furnishes a scaffold for inducible cell attachment and proliferation and mineral deposition. The given geometry and mechanical integrity make the preparation ideal for filling bone defects in weight-bearing sites. Probably calcium ions released from dissolution of Ca-dominant ceramics in the composite preparations also played an active role in the regulation and expression of BMP bioactivity.

The composite preparation natural coral-collagen-BMP upgraded the osteoinductive potential in comparison to tricalcium-collagen-BMP as shown in the experimental part of this specification. $^{45}$Calcium uptake, the newly formed bone in radiography and new bone ingrowth to the pores in histology were greater in the natural coral-collagen-BMP than in the tricalcium phosphate-collagen-BMP preparation. Differences were considered to be mainly the variances in ingredients and resources between the two ceramics used in the composite carriers.

Calcium carbonate in the structure of orthorhombic crystalline termed aragonite accounts for 97% of natural coral. After natural coral was implanted in vivo, a rapid surface modification took place before new bone was apposited. Initial dissolution of the surface released calcium and carbonate ions into the surrounding fluid and then the precipitation or deposition of a layer of calcium-phosphate and/or a conversation of carbonate surface layer to carbonate-calcium phosphate occurred. The calcium-phosphate rich layer on natural coral was a critical structural basis for both new bone apposition and cell-mediated degradation. It has been established that natural coral skeleton is perfectly biointegrated and also has slight osteoinductive properties. Consequently, a higher $^{45}$Ca incorporation in the controls of natural coral with or without collagen than with tricalcium phosphate with or without collagen provides evidence of the osteogenic effect in the early stage after implantation. Another important fact is that natural coral is obtained from the natural mineral skeleton of scleractinian corals, whose structure is different from the man-made tricalcium phosphate.

Natural origin and architecture enable coral to assimilate more BMP, regulate BMP biofunction and attract more osteoprogenitor cells.

The mechanism in detail remains to be elucidated. Since natural coral exhibited a better bioresorbability, mechanical resistance and BMP delivery efficacy, it is probably one of the ideal alternatives for BMP carriers from the clinical view point.

Dose-dependent bone formation is an important yardstick of the biological properties of BMP. Quantities of induced bone increased in proportion to the doses of moose BMP added to the composite preparation. $^{45}$Ca uptake in the composite preparations with 4 mg moose BMP for example was much less than that with 8 mg moose BMP on both the 10th and 20th day. The dose-dependent bone induction of mBMP with ceramics and the collagen does not interfere with the biological function of moose BMP.

More intensive osteoinduction was elicited by the composite preparations, moose BMP with or without type IV collagen at 10 days than at 20 days. The reason for this extraordinary phenomenon remains obscure. Since no agreement has been reached on how the combination of BMP with ceramic carrier can speed up or slow down the time sequence of bone induction, the combination method involving triple components in this study might facilitate the expression of BMP phenotype and bone formation.

The complications of homo- and heterodimeric forms presented in the polypeptide complex of BMP might increase, decrease or even inhibit activities in the bone induction system. The immunological problem initiated by implantation of heterogenic BMP can also be manifested in the infiltration if inflammatory reactive cells around the preparations charged with moose BMP in different groups. The bioactive entity of moose BMP complexes qualified with multiple fractions of different molecule weight contributed to its osteoinductive potential as well as immunogenetic initiation, which interrupted or decreased osteoinduction by the 20th day after implantation. The events involved in immunogenecity of different dissociated fractions of moose BMP are currently under research.

Intensive research on BMP has opened a new frontier for the development of bioactive bone substitutes. BMP, the glycoprotein especially lodging in the matrix of hard tissue, plays an important role in both chondrogenesis and osteogenesis of embryonic as well as postfetal life. Large unhealed bone defects have been successfully repaired by naturally occurring BMP when the BMP was carried by a suitable delivery system. Using partially purified human BMP conveyed by autogeneic bone grafts or autolyzed antigen-extracted allogeneic bone in the management of resistant femoral nonunions encouraging preliminary results were achieved, but limited sources of autogeneic cancellous grafts in the patients was still a frustrating problem.

Some bioceramics have been used as carriers of BMP in experimental studies. Established porosity, mechanical integrity and tissue compatibility qualified some of these bioceramics as possible carriers of BMP. The key point in remaining problems is how to combine BMP, a biological factor, with ceramics, inorganic substances, effectively and to retain or even modulate the biological function of BMP in reconstitution.

Using tricalcium phosphate cylinders impregnated with sheep BMP and type IV collagen, the potentiation of this composite bone substitute in the repair of segmental bone defects in the tibia of sheep was established. The present subclinical study aimed at persuing the possibility and prospects of developing a bioactive bone substitute for clinical application.

The most practical application of BMP research is treatment of patients with intractable non-union of fractures and large bone defects. Bridging the gap between basic research and clinical application of BMP has been the objective of many investigators and clinicians for two decades. The critical point of successfully managing large bone defects, especially in weight-bearing limbs, is to reconstruct to bony continuity with an established mechanical integrity and to facilitate local bone regeneration simultaneously.

The mechanical integrity of the implant reinforces immobilization of the defect site at an early stage and provides a scaffold for osteogenic tissue. The motivated osteogenecity secures the healing of the defect. The development of bioceramics to date has supplied a wide range of biocompatible bone-filling materials for clinical application, but no bioceramic has been reported with definitive osteoinductivity.

With naturally occurring or human recombinant BMP, large bone defects in rat, rabbit, canine, sheep models and humans have been successfully repaired when the osteogenic proteins were combined with collagen derivatives, polylactic acid and autolyzed antigen-extracted allogeneic (AAA) bone, respectively. However, lack of desirable geometry and mechanical integrity in these BMP carriers still made the composite implants inaccessible for surgery.

By using the composite bone substitute consisting of triple component, tricalcium phosphate charged with naturally occurring BMP and type IV collagen, our experimental results demonstrated, to our knowledge for the first time, that this bioactive composite bone substitute has a profile of mechanical strength as well as the capacity to induce a segmental diaphyseal defect healing in sheep.

An appropriate delivery system performs several essential functions for osteoinduction of BMP, including restrictive release of BMP at the effective dose during a period coincident with the accumulation and proliferation of target cells and accommodating each step of the interaction between the cells and bone formation. The material must be biocompatible and biodegradable, and it should provide a substrate for attachment of recruited osteogenitor cells.

A tricalcium phosphate disc as a carrier of bovine BMP was described by Urist et al., Clin. Orthop. 187, 277–280, 1993. After 21 days of implantation, a 12-fold quantity of new bone was produced in an implant of tricalcium phosphate-BMP compared to an implant of 1.0 mg BMP alone in mouse muscle pouches. The potential effect of Type IV collagen on the osteoinductivity of bovine BMP has been evidenced in our previous study.

The working hypothesis on which we reconstituted the composite bone substitute with triple components in this experiment was that the mechanical integrity, biocompatibility, porosity and availability for binding BMP in a tricalcium phosphate cylinder combined with the potentiation of type IV collagen in the osteogeneic capacity of BMP would make the composite bone substitute more accessible for clinical application.

Experimental results have demonstrated a difference in extent of bridging callus between composite bone substitute with 100 mg sheep BMP and composite bone substitute with 13 mg sheep BMP or tricalcium phosphate with Type IV collagen from 3 weeks and became obvious at 6 weeks after implantation. It confirmed that the cascade of bone formation induced by BMP was usually expressed from 7 days to 4 weeks depending on different animal species, carriers and implant sites. Since the periosteum was preserved in the study, more activated mesenchymal-type cells and inducible cells from the cambium layer of the periosteum or endosteum contributed to an earlier exuberant bone regeneration surrounding the BMP-impregnated implants in sheep tibia.

Compared to repair of a segmental defect in a sheep femur with recombinant BMP, formation of bridging callus appeared earlier in our study. A significantly larger area and more highly integrated intensity of the bridging callus in composite bone substitute (CBS) with 100 mg sheep BMP than in composite bone substitute with 13 mg sheep BMP or tricalcium phosphate cylinder implants has been defined by computerized image analysis in both 3 and 6 weeks.

Dose-dependent bone induction of BMP was one of notable biological characteristics. It is generally known that the higher the species of animal and the larger the defect created, the more BMP is needed to heal the defect. Without significant statistically differences in area and integrated intensity of the callus at different times and in mechanical strength between composite bone substitute with 13 mg sheep BMP and tricalcium phosphate cylinders, in the experiments of the present invention also demonstrated that healing large bone defects in higher mammals requires a large dose of BMP.

The distributions and shapes of bridging callus around the BMP-impregnated tricalcium phosphate and BMP-free tricalcium phosphate implants revealed a clear difference especially at 6 weeks. This interesting phenomenon may provide further evidence of the local effect of BMP on osteoinduction. In accordance with the increase in the amount of bridging callus in composite bone substitute with 100 mg sheep BMP in the early stage, the accumulated density of the callus was significantly augmented in a computerized tomography (CT) scan at the end of the experiment. This increment showed that more mature callus and mineral content were generated in composite bone substitute with 100 mg sheep BMP than tricalcium phosphate cylinders. The correlation of extent of area of the bridging callus in the early stage with the increment of density of the callus at the later stage in BMP-impregnated implants might imply that BMP also promotes the process of bone remodelling.

Mechanical strength has been established as the gold standard for the biological healing of fracture in experimental studies. The torsion test was thought to be a comprehensive and reliable parameter of bone strength. In the composite bone substitute groups, all the parameters of torsion test were enhanced as the sheep BMP dose in the composite implant was increased in comparison to tricalcium phosphate cylinders group. In spite of the stress-shielding effect of rigid immobilization by two overlapped AO plates, the osteotomized tibia with an implant of composite bone substitute with 100 mg sheep BMP was even stronger than the contralateral tibia with coinciding holes.

Large standard deviations of torsion test parameters were also encountered in our study, but a significantly increased percentage of bone stiffness against the contralateral tibia was still revealed in the healed osteotomized tibia implanted with composite bone substitute with 100 mg sheep BMP in comparison to that with of tricalcium phosphate cylinders at 16 weeks. Since composite bone substitute not only enriched formation of bridging callus but also induced new bone ingrowth in the pore of tricalcium phosphate, good osteointegration was observed between new bone and composite bone substitute implant histologically. The fact that the fracture line in mechanical testing passing through the implant-bone interface occurred in only one of 6 the composite bone substitute with 100 mg sheep BMP also provided evidence of good osteointegration.

Established osteointegration and remodelling, anchored tricalcium phosphate cylinders in the defect and extended observation time were explained to be contributions of increased bone stiffness in the composite bone substitute with 100 mg sheep BMP group. Gross spiral fracture patterns were also consistent with the biomechanical stage of healing. In torsion test the contralateral tibia in which coinciding holes had been made were used as self-control for evaluating the relative strength of healed tibia. The idea was to create a duplicate testing condition and reduce the variances of the means of parameters that stemmed from influences of differences in body weight and age on bone strength. However, the reducing effect of sheep tibia with holes on the mechanical performance of intact tibia remains to be illustrated.

In conclusion, the composite bone substitute with triple components provided the advantages of osteoinduction, osteoconduction and mechanical resistance. Nowadays advances in biomaterials research have provided better possibilities to screen for an appropriate biomaterial as skeleton for composite bone substitute. The limited sources and impurity of naturally occurring BMP could be circumvented by the preparation of recombinant BMP. With the development of reconstitution techniques, a desirable composite bone substitute for human being will be available. The most substantial relevance in this experimental study was to highlight the necessity and advantages of developing a synthetic bioactive bone substitute for medical practice.

It is not only a great challenge for mankind to develop new and improved delivery systems for BMP which can be used in the treatment of patients with skeletal disorders and deformations. It is also important to improve the properties of the components used in the osteogenic devices.

Bone morphogenetic protein BMP is generally isolated with methods developed by Urist et al.; In Lindholm TS (ed): New Trends in Bone Grafting. Acta Universitatis Tamperiensis, University of Tampere, 1992, ser B vol. 40, pp. 27–39, Urist et al., PNAS 76, 1828–1932, 1979, etc. BMP, its isolation, purification and properties are also described e.g. in the following patents U.S. Pat. No. 5433, 751, U.S. Pat. No. 4,294,753, U.S. Pat. No. 4,455,256, U.S. Pat. No. 4,563,489, U.S. Pat. No. 4,596,574, U.S. Pat. No. 4,789,732 and U.S. Pat. No. 4,795,804.

The extraction methods developed by Urist et al. are used today in most laboratories and are characterized by the use of guanidinium hydrochloride (GuHCl)-extraction and further characterized by the following features. The bone matrix is first ground and gelatinized in order to release proteins of non-collagenic origin. The extraction is performed in the presence of calcium chloride and protease-inhibitors. Lipids, which disturb the purification process are removed from the raw material. Thus, the BMPs obtainable by the conventional laboratory methods from native bone matrix are gelatinized and essentially lipid free. They might contain traces of proteinase inhibitors as well as a surplus of $Ca^{++}$-ions.

The bone morphogenetic protein has also been prepared by recombinant DNA techniques. Such methods are disclosed e.g. in the patent publications WO 90/11366 and WO 95/24474. Said rhBMP is free from any remnants, residues or rests from the native bone matrix, which might remain attached to the native BMP after the extraction with the methods generally used. rhBMP lacks for example lipids and other substances possibly present in of the natural bone derived BMP.

The inventors of the present application unexpectedly found that if the conventional laboratory methods are somewhat modified a new type of BMP is obtained. Said new type of BMP, i.e. the modified BMP complex (mBMPc) of the present invention, combined with collagen and shapable carriers, such as bioceramics including biocorals gave surprisingly good bone formation results.

Native BMPs extracted by methods differing from that of the present invention have not proved to be as effective as the mBMPc extracted with the method of the present invention in combination with the carrier materials used in the osteogenic device of the present invention. But it is not only the carrier material which is important in the bioresorption of bone. The type of the BMP complex used and its properties are very important in order to obtain the desired osteoinductive properties.

The inventors have obtained the best results which mBMPc, which indicate that gelatinized BMP or rhBMB lacks some essential components, which are essential to achieve a good implant. The inventors have consequently found that surprisingly good osteoinductive properties can be achieved with an osteogenic device which includes a modified BMP complex isolated with a modification of the Urist methods which is defined in the claims in combination with type IV collagen and a biocoral carrier.

Consequently, in the preferred embodiment of the present invention the BMP is extracted with methods described by Jortikka, L. et al. (Ann. Chir. Gynaecol. 82: 25–30, 1993) and Jortikka et al. (Ann. Chir. Gynaecol. 82: 31–36, 1993). Said methods are based on the method described by Urist et al.; In Lindholm TS (ed): New Trends in Bone Grafting. Acta Universitatis Tamperiensis, University of Tampere, 1992, ser. B vol. 40, pp. 27–39. The essential differences between the extraction methods of Urist and that used for the preparation of the modified BMP complex used in the osteogenic device of the present invention are listed below.

In the method of the present invention the ground bone matrix is not gelatinized, because the inventors have noticed that the separation, detachment, loosening or release of non-collagenic proteins using guanidinium-HCl (GuHCl) is as effective without gelatinization as with gelatination. Thus a non-gelatinized product is obtained. It is possible and sometimes advantageous but not necessary to use collagenase in the extraction process.

Another distinguishing feature is that in the method of the present invention calcium chloride is not used in connection with the GuHCl-extraction and consequently the chelatinizing effect of $Ca^{++}$-ions is missing in the extraction procedure. Thus, no surplus of $Ca^{++}$-ions are present in the product obtained by the method of the present invention.

Furthermore, the inventors have noticed that proteases are not active in 1.5–5.0 M, preferably 4 N GuHCl. Thus, proteinase inhibitors are not used in the extraction steps of the present invention and a modified BMP complex is obtained which does not contain any proteinase-inhibitor residues (traces), which might be harmful or detrimental to the patient.

Because a tangential ultrafiltration apparatus is used no lipid extraction is needed. The action of said apparatus is not disturbed by lipids and consequently the removal of lipids before concentrating can be avoided. Because the last stage in the preparation of the crude product is HPCL gel filtration, there is no need to remove other protein molecules with a dilute GuHCl solution in the intermediate stages of the extraction procedure. Of the same reason a Triton X-100 extraction is not needed.

The last and essential stage in the production of the crude preparation is HPLC gelfiltration, in which three separate fraction are obtained. These distinguishable fractions are called Fraction I, II and III. Fraction I contains a high MW (100–700 kD) protein. Fraction II contains a medium MW (25–55 kD) protein and Fraction III contains a low MW (15–25 kD) protein. The medium MW (25–55 kD) Fraction II causes apparent inflammatory reactions and no bone formation. Because said Fraction II seems to be immunogenic it is discarded and not used. The other two fractions obtained by the HPCL gelfiltration, Fraction I, i.e. the high MW MBP fraction and Fraction III, i.e the low MW MBP fractions are collected.

Said two fractions can be used separately. Especially preferred for its good storability is Fraction III. Optionally the Fraction I and III are combined (mixed) and said partially purified preparation can be used as such or further purified with preparative isoelectric focusation or by preparative SDS-PAGE (BioRad apparatus). In clinical treatment use of partially purified preparations seems to have the best osteoinductive properties.

Consequently, the modified BMP complex, obtainable by the method described above is a non-gelatinized, non-collagenic, non-chelatinized, lipid-containing protein complex comprising a mixture of at least two different MW (100–700 kD and 15–25 kD) BMPs and the complex lacks the immunogenic 25–55 kD fraction. The crude preparation can be freeze-dried, sterilized and has a prolonged storability.

The preparation can be used directly to prepare the osteogenic devices of the invention, but it also possible to revive the freeze-dried BMP preparation and use it after storage for preparing the osteogenic device of the present invention.

The non-collagenous, water soluble bone morphogenetic protein (BMP) material obtainable by the method described above is mixed with soluble collagens, preferably Type IV collagen or Type I collagen and is used to impregnate natural biocoral, which might optionally be used in combination with hydroxyapatite, bioactive glass or other suitable carrier materials.

The invention is described in more detail in the following examples and experiments. It should be understood that the examples and experiments are only intended to illustrate the invention in more detail and should not be construed as limiting the scope of the protection.

EXAMPLE 1

Purification of Osteoinductive Polypeptides, BMP from Bovine Cortical Bone

The starting material for isolation of osteoinductive polypeptides, such as bone morphogenetic proteins (BMP) was cortical bovine bone, controlled and approved by district veterinarians before use. Immediately after death of the animals the long cortical bones were removed and chilled and kept in cold until extraction process was started. The BMP purification was started within 30 hours.

The cortical bovine bone material was pulverized into 1–2 $mm^3$ particles and demineralized in 0.6 N HCl. Noncollagenous proteins were extracted from the demineralized bone particles in 4 M guanidinium hydrochloride (GuHCl). The protein material soluble in GuHCl was dialyzed against water and water-insoluble material was collected. This material was again dissolved in GuHCl and undissolved material discarded. Finally the GuHCl with the protein material was dialyzed against 0.2 M citrate buffer, pH 3.1.

Citrate buffer insoluble material was gel filtrated and fractions containing osteoinductive polypeptides, BMPs were pooled and fractionated using preparative SDS PAGE. Again, osteoinductive fractions were pooled and further fractionated using HPLC reversed phase chromatography. As a result, 3 distinguishable polypeptides could be collected (FIG. 1, FIG. 2).

Biological testing of osteoinductive BMP properties of the fractions was performed in a mouse muscle pouch assay which showed the capability of new bone formation. For details of the bioassay procedure see Example 4.

Two osteoinductive polypeptides fractions with BMP activity were found and said fractions, Fraction I and III were combined and precipitated with water and washed twice in distilled water. Alternatively, the same procedure was performed with Fraction III alone. Finally, the material was washed with sterilized water during aseptic conditions and stored in −20° C.

EXAMPLE 2

Preparation of Partially Purified Osteoinductive Polypeptides with BMP Activity from Premature Moose (Alces alces)

A total of 102 kg of fresh long bones from premature moose (Alces alces) claves were chilled no later than one day after the death of the animals. The epiphyses, periosteum and bone marrow were mechanically removed. After freezing in liquid nitrogen the cleaned cortical bone was sawn and ground to particles of 0.5–1.0 mm³.

Pulverized bones were demineralized in 0.6 mol/l HCl for 72 hours and extracted in 4 mol/l guanidium-HCl (GuHCl) for 96 hours without defatting or gelatinization of demineralized bone matrix. The GuHCl-extracted solution was filtrated through a 0.30 µm filter by tangential flow system and ultrafiltrated through a filter with a cut-off point of 10 kD (Minitan, Millipore, Md., USA).

The concentrated GuHCL solution containing BMP complex was dialyzed against water for 24 hours and the water insoluble material was again dialyzed against seven volumes of 0.25 mol/l citrate buffer, pH 3.1. Thereafter a total of 5.85 g of partially purified moose BMP was harvested from the citrate buffer-insoluble material after lyophilization at the end of the process.

The recovery of partially purified moose BMP was 57.35 mg/kg of fresh bone. The preparation procedure used here was a modified from a method previously described by Jortikka, L. et al., Clin. Orthop. 1993; 297:33–37 and Urist et al.; In Lindholm TS (ed): New Trends in Bone Grafting. Acta Universitatis Tamperiensis, University of Tampere, 1992, ser B vol. 40, pp. 27–39.

EXAMPLE 3

Characterization of Partially Purified Osteoinductive Polypeptides with BMP Activity from Premature Moose To characterize partially purified moose BMP, 120 mg of the lyophilized preparation was dissolved in 1 ml of 6 mol/l urea and chromatographed using Sephacryl$^R$ S-200 HPCL gel filtration column. The chromatogram is shown in FIG. 1. The eluted fractions were collected and compared with the molecular weight markers of thyroglobulin, β-amylase, alcohol dehydrogenase, ovalbumin, carbonic anhydrase and myoglobin. Collected fractions were lyophilised separately for further characterization and bioassay.

20 µg of lyophilized Fractions I and III, shown to have bone-inducing activity in the mouse thigh muscle bioassay (See Example 4 below), were treated with sodium docdecyl sulfate (SDS) and applied on 1-mm polyacrylamide isolelectric focusing gel (pH range 3.5 to 9.5) for determination of isolelectric focusing points of proteins. An isolelctric focusing calibration kit was used as standard (Pharmacia AB, Uppsala, Sweden). The gel was stained with 0.005% Coomassie brilliant blue. The isolelectric points for the Fraction I and III, which evidenced BMP activity in the mouse thigh muscle bioassay, ranged from 5.3 to 5.6 in reduced conditions.

EXAMPLE 4

Bioassay of BMP

To characterize partially purified BMP by HPLC gel filtration, 0.5 mg of BMP was dissolved in 2.0 ml of 4 M GuHCl and applied to a 300 mm-length Sepharyl 200 HPLC chromatographic column (Pharmacia Diagnostics, Sweden). Eluted fractions were automatically collected and compared with the standard proteins in the absorbance at 280 nm. After dispersion in N 0.5 gelatin capsules, 0.5, 1, 2, 5, 10, 15 mg of the partially purified BMP were separately implanted in muscle pouches in the hinds of BALB mice for bioassay. 10 and 21 days after implantation, ectopic new bone formation was evaluated by roentgenography and histology.

Bioassays of semipurified BMP were-made immediately after the extraction procedure and repeated fifteen months thereafter, when also fractionation and bioassays for Fractions I–III, and isolelectric focusing were carried out.

EXAMPLE 5

Preservation of BMP

The extracted and lyophilized material was preserved in dry state in dry sterile closed glass tubes in a desiccator at +1° C.

EXAMPLE 6

The Preparation of the Osteogenic Device

Impregnation BMP with Collagen

Water-soluble purified BMP was prepared as described above. Commercially available type IV collagen (Sigma Corp. NO. C 5533 from basement membrane of human placenta) or atelopeptide type I collagen (Nitta Gelatin Inc. Osaka, Japan) and Lyostypt$^R$ (B. Braun Meisungen AG, Germany) are the alternatives of collagen for human use.

Water-soluble purified BMP and collagen are dissolved in NaCl at room temperature and the mixture is incubated at 4° C. for 12 hours, to allow BMP to bind completely with collagen.

EXAMPLE 7

The Preparation of the Osteogenic Device

Adsorbing BMP Impregnated Collagen to a Carrier

As the porous substratum or carrier approved bioceramics for human use are required. Alternatively human demineralized cortical bone can be used. If human bone material is used, it must be tested and accepted by the Bone Bank System at the Department of orthopedics and traumatology, University Hospital of Tampere, Finland. In such cases the demineralization of human bone material by 0.6 N HCl and further processing is performed according to conventional methods described in literature.

Among the approved bioceramics approved for human use, which bioceramics can be used as the skeletons in the ostegenic devices the following materials can be used either as such or in suitable combinations:

(1) Biocoral$^R$ (Inoteb Corp., Saint Gonnery, France);
(2) hydroxyapatite (Bioland Corp, Toulouse, France);

(3) tricalcium phosphate (Skeleton Repair System, Norian Corp., California, USA;
(4) tricalcium phosphate (Howmedica, Warsaw, USA); and
(5) bioactive glass.

The adsorption of the BMP-impregnated collagen to the porous substratum or carrier blocks proceeds using the following steps:
(1) The carrier block was immersed into a mixture solution of BMP impregnated collagen in a container and placed into a vacuum oven at 25–30° C. until all bubbles were released from the substratum. The container with the BMP impregnated collagen solution further containing the immersed carrier blocks were kept at 4° C. for 6 hours in order to entrap more BMP in the porous substratum or carrier.
(2) The solution mixture with the porous substratum block was poured into dialysing tubes (cut-off of 12,000–14,000 daltons) and they were dialyzed against 10 mM glycine buffer, pH 5.9, stirring at 4° C. for 24 hours.
(3) After the dialyzing was completed, the blocks were removed from the dialysing solution to a plastic, shape-fit model, which was prepared in various sizes and forms to fit the dimension of carrier blocks, and finally the dialyzed solution was centrifuged (3,200 rpm for 20 min).
(4) The supernatant of centrifuged solution containing no BMP impregnated collagen was discarded and then the individual carrier blocks in the shape-fit model were coated with aliqouts of resuspended precipitate, which contains some remnants or debris of BMP impregnated in centrifuge vials.
(5) The osteogenic devices in the plastic shape-fit models were lyophilized.

The dosage of BMP and collagen in the prepared osteogenic device was countered as microgram per cubic centimeter of carrier. It corresponded to 100 μg BMP and 500–1000 μg collagen/cm$^3$ of carrier.

EXAMPLE 8

Reconstitution of Composite Implants

The tricalcium phosphate cylinders (B 247, DePuy, Warsaw, Ill., USA) and natural coral rods (Biocoral$^R$, Inoteb, Saint-Gonnery, France) were commercially available biomaterials which bear an architectural resemblance to human bone. The porosity of tricalcium phosphate and natural coral ranges from 20 to 50% and the pore size from 150 to 500 microns with enriched interconnecting channels. The ceramics were machined to discs 4 mm in diameter and 2 mm thick. Type IV collagen (Sigma, St. Louise, Mo., USA) was dissolved in 0.25 M HCl containing 0.5 M NaCl, dialyzed against water and centrifuged to remove impurities.

Partially purified mBMP and dialyzed type IV collagen in ratio of 4 to 1 were redissolved in 4 M GuHCl solution and incubated in 20° C. overnight. Then the tricalcium phosphate and natural coral discs were immersed in the mixture solutions which contained high or low moose BMP concentration respectively. The triple mixture solutions were dialyzed against ten volumes of 10 mM glycine buffer, pH 5.9, with stirring for 24 hours. The mixture solutions were centrifuged at 3,200 rpm after the tricalcium phosphate and natural coral discs were transferred into individual small tubes. The aliquot of precipitate in the centrifuge vials was dispersed into small tubes containing the tricalcium phosphate or natural coral disc. The tubes were placed in lyophilization for 48 hours.

Each composite preparation natural coral-collagen-BMP, tricalcium phosphate-collagen-BMP contained 8 mg of moose BMP in the high dose group and 4 mg of BMP in the low.

Using the same procedure, combinations of BMP, tricalcium phosphate and natural coral with type IV collagen (collagen-BMP, tricalcium phosphate-collagen and natural coral-collagen) were prepared as carrier controls. Moose BMP, tricalcium phosphate and natural coral alone were used as the component controls. All the implants were exposed to ethylene oxide for sterilization before implantation.

EXAMPLE 9

Sterilization and Storage of the Osteogenic Device

For sterilization of the device several conventional methods are available. However, some of them eg., gamma-radiation is not approved in some countries and sterilization by heat is not acceptable because of denaturation of proteins.

Consequently, the osteogenic device is sterilized by ethylene dioxide gas for 2 hours in a sealed sterilizer and evaporated in ventilation for 2–3 hours.

EXAMPLE 10

Preparation of Composite Bone Substitute for Sheep

The tricalcium phosphate cylinder was a commercially available bioceramic which bears an architectural and chemical resemblance to human bone. The shaped cylinders were 15 mm in diameter and 16 mm in length with a plug 3 mm in length at the each end. A central hole 4 mm in diameter was drilled longitudinally in order to reproduce a medullary canal. Type IV collagen was dissolved in 0.25 M HCl solution containing 0.5 M NaCl and dialyzed to remove impurities. The bone morphogenetic protein extracted chemically from the fresh tibia and femurs of sheep by 4 M GuHCl in our laboratory was partially purified through a 0.65 μm filter by a tangential flow system, dialyzed and lyophilized.

The minimal dosage of partially purified sheep BMP, which was extracted as described above in example 1, which induced radiologically detectable ectopic bone formation in muscle pouches of BALB mice was 4.8 mg at 3 weeks after implantation. Sheep BMP in high or low dosage and purified collagen Type IV were dissolved in 4 M GuHCl solution in a ration of 5 to 1 and incubated at 20° C. overnight. The tricalcium phosphate cylinder was immersed in the mixture solution and then dialyzed against ten volumes of 10 mM glycine buffer, pH 5.9 for 24 hours. Centrifugation of the dialyzed mixture solution was carried out after the tricalcium phosphate cylinder was transferred into a plastic shape-fit mold.

The precipitate containing the remnant of sheep BMP in the centrifuge vial was coated on the surface of the corresponding tricalcium phosphate cylinder in the mold. After lyophilization each composite bone substitute contained 13 mg of sheep BMP in the low dose group composite bone substitute (CBSL) and 100 mg of sheep BMP in the high dose group composite bone substitute (CBSH). The tricalcium phosphate cylinders impregnated with a corresponding dose of type IV collagen alone were prepared by the same procedure as control. All prepared implants were exposed to ethylene oxide for sterilization before implantation.

Experiment 1

The Bone-Inducing Activity of Partially Purified Moose BMP and Fractions I, II and III The bone-inducing activity of partially purified moose BMP and Fractions I, II and III from the Sephacryl$^R$ S-200 gel filtration (FIG. 2) were bioassayed in BALB mice aged 28 to 35 days. Capsules with different doses were separately implanted in bilateral thigh muscle pouches in the mice.

Experiment 2

Results of New Bone Formation in Mice Using the Modified Osteoinductive BMP Complex Shortly after extraction of the moose BMP obtained in Example 2, ectiotopic new bone formation in muscle pouches was radiographically and histologically detectable at a dose of 2 mg of BMP 21 days after implantation. As the dose of partially purified moose BMP increased from 5–10 mg, the amount of newly formed bone was partially augmented in the radiographs at 21 days. However, there was no further increment of newly formed bone with 15 mg of BMP. Histological analysis revealed that the newly formed tissue comprised mostly an-ossicle of woven bone with bone marrow.

When the bioassay was repeated after 15 months with purified BMP, only a small amount of ectopic calcified tissue was detected in radiographs compared to the first bioassays, and then, at 21 days after implantation, the amount and density of calcified tissue were clearly reduced compared to those with corresponding doses at 10 days. Histological analysis revealed a patch of cartilage at 10 days and a small island of woven bone at 21 days after implantation. More inflammatory cells were observed round the newly formed bone at 21 days than at 10 days.

The yield after the gel filtration consisted of three protein fractions with different molecular weights (FIG. 1). Fraction I, II, and III were defined with molecular weights 700–100, 55–25 and 25–15 kD, respectively. The isolelectric points of fraction I and III, which showed BMP activity in the mouse thigh muscle bioassay, ranged from 5.3 to 5.6 in reduced condition. Three different protein bands could be distinguished between this pI range in both fractions with BMP activity. The two bone-inducing fractions of moose BMP were acidic proteins after one-step fractionation.

Radiographically visible ectopic bone formation was induced in this experiment by 4.5 mg of BMP fraction I and 5.5 mg of Fraction III. The amount and density of ectopic bone induced by the same dose of Fractions I and III were radiologically greater at 21 days than at 10 days, in contrast to partially purified BMP after fifteen months from extraction.

Histologically BMP Fractions I and III induced fully developed cartilage in 10 days and an initial transformation of cartilage to woven bone could be seen. A complete ossicle with normal bone marrow tissue developed in 21 days. More advanced remodeling of newly formed ossicle was observed with Fraction I than with Fraction III in 21 days after implantation. There was almost no infiltration of inflammatory cells with Fractions I and III both 10 and 21 days. in contrast to partially purified moose BMP or Fraction II.

Fraction II initiated a radiographically visible patch of ectopic calcification in 10 days but this diminished by 21 days after implantation. Microscopy of the samples revealed that the calcifications were composed of a patch of granular crystal substance without bone or cartilage architecture.

Large amounts of inflammatory cells around the crystals expressed a severe inflammatory reaction. No trace of new bone formation was noted microscopically by 21 days after implantation. Compared to partially purified BMP complex in identical doses after fifteen months of storage, Fractions I and III induced ectopically more mature new bone at an earlier stage and at the same time less inflammatory reaction.

However, the bone-inducing activity of partially purified BMP initially after extraction corresponded well to the activity of Fractions I and III form the gel filtration performed at 15 months.

Experiment 3

Osteoinductive Potential of Moose BMP and Type IV Collagen Impregnated Natural Coral and Tricalcium Phosphate Ceramics Determined in Mice By using partially purified moose bone morphogenetic protein obtained by the method described in Example 2 and Type IV collagen impregnated natural coral and tricalcium phosphate ceramics, the osteoinductive potential of the composites was established by $^{45}$Ca incorporation in BALB mice. The composite implants were prepared by a combined method of dialysis with coating.

132 BALB mice were divided into 12 experimental groups depending on the different components and dose of moose BMP in the composite (See Table 1). $^{45}$Ca incorporation in the different composite preparations was notably superior to the collagen-BMP and BMP alone (p<0.01). The highest peak of $^{45}$Ca incorporation took place in the natural coral-collagen with 8 mg mBMP at the 10th day. It was significantly higher than the tricalcium phosphate-collagen with 8 mg moose BMP, collagen-BMP and BMP alone.

TABLE 1

Grouping of experimental mice and implanted materials in muscle pouch

| Group | Implants | BMP content | Number of mice |
|---|---|---|---|
| Test | NC/COL/BMP | 8 | 14 |
|  | NC/COL/BMP | 4 | 14 |
|  | TCP/COL/BMP | 8 | 14 |
|  | TCP/COL/BMP | 4 | 12 |
| Control | COL/BMP | 8 | 12 |
|  | COL/BMP | 4 | 10 |
|  | BMP | 8 | 10 |
|  | BMP | 4 | 10 |
|  | NC/COL | — | 8 |
|  | NC | — | 8 |
|  | TCP/COL | — | 8 |
|  | TCP/COL | — | 8 |
| Total | 12 |  | 132 |

Ectopic new bone formation was evaluated by radiography (100 mA, 20 kV, 0.08s/exp; Mamex de Maq, Soredex. Orion Corporation Ltd) and histological sections stained with hematoxylin-eosin and azure II at 10 and 21 days after implantation.

The difference was also manifested between the paired composite implants with identical components charged with 8 and 4 mg moose BMP at both the 10th and 20th day (p<0.01). The composite carriers, natural coral-collagen and tricalcium phosphate-collagen, up-regulated the osteoinductive potential of BMP. The natural coral-collagen-BMP composite has even more powerful bone inductivity than the tricalcium phosphate-collagen-BMP composite. The multiporous architecture, given geometry and different chemical properties of the ceramics combined with the biological modulations of Type IV collagen to BMP probably enhance the local effect of BMP on inducable cells.

Experiment 4

Implantation and Analytic Methods

One hundred and thirty-two BALB mice aged 28–32 days were divided into 12 experimental groups. Independent variables included the presence of composite implants or carriers alone, moose BMP with or without collagen and natural coral or tricalcium phosphate alone. Implantation was performed in muscle pouches bilaterally in the hind of the mouse. Grouping of animals and implanted materials are summarized in Table 2. The observation time was 10 and 20 days.

TABLE 2

$^{45}$Ca Incorporation into implants and ectopic new bone formation on X-ray films

| Implants | BMP (mg) | Samples (No.) | $^{45}$Incorp. (DPM/mg) 10 Days | 20 Days | New Bone Format.* 10 Days | 20 Days |
|---|---|---|---|---|---|---|
| NC/COL/BMP | 8 | 24 | 28.06 ± 2.83 | 13 ± 5.47 | 12/12 | 8/12 |
| NC/COL/BMP | 4 | 24 | 21.98 ± 6.67 | 8.99 ± 5.38 | 12/12 | 9/12 |
| TCP/COL/BMP | 8 | 22 | 19.45 ± 3.05 | 6.41 ± 1.43 | 10/10 | 10/12 |
| TCP/COL/BMP | 4 | 24 | 16.32 ± 2.57 | 3.32 ± 0.67 | 12/12 | 7/12 |
| COL/BMP | 8 | 16 | 6.09 ± 0.43 | 4.93 ± 0.49 | 8/8 | 2/8 |
| COL/BMP | 4 | 16 | 2.97 ± 0.82 | 1.26 ± 0.15 | 8/8 | 2/8 |
| BMP | 8 | 16 | 5.60 ± 0.24 | 5.80 ± 0.04 | 6/8 | 4/8 |
| BMP | 4 | 12 | 2.97 ± 0.82 | 1.99 ± 0.47 | 3/4 | 0/4 |
| NC/COL | — | 8 | 1.85 ± 0.04 | 0.81 ± 0.17 | 0/4 | 0/4 |
| NC | — | 10 | 2.86 ± 0.45 | 1.25 ± 0.23 | 0/6 | 0/6 |
| TCP/COL | — | 10 | 0.85 ± 0.09 | 2.11 ± 0.43 | 0/4 | 0/6 |
| TCP | — | 8 | 0.68 ± 0.14 | 2.60 ± 0.43 | 0/4 | 0/4 |
| Total | | 190 | | | 71/92 | 46/98 |

*Osteoinductive rate: No. of positive samples/No. of implants.

The meaning of abbreviations within the table are explained in the text.

Twenty-four hours before being killed each mouse was given an intraperitoneal injection of diluted carrier-free $^{45}$Calcium solution (Amersham, England) in 4 μCi/kg of body weight. The dissected hinds with implants were X-rayed by mammography (100 mA, 20 KV, 0.06 Sec.) before sampling. The tissue including implant and newly formed bone was taken en bloc as a specimen.

A piece of the muscle and femur in the hind were taken as reference for $^{45}$Ca incorporation in different tissue originating from the same animal. All specimens were weighed and digested in a mixture of 0.2 ml 70% perchloric acid and 0.4 ml 33% peroxide, 70° C., for 3 hours (Mahin et al., Anal. Biochem. 16, 500–509, 1966). Then 0.6 ml digested solution was pipetted into a diffuse scintillation vial and 5 ml scintillation cocktail (OptiPhase'Hi-Safe 3', Wallac, England) was added.

Homogenous samples were counted in a liquid scintillation counter (Wallac 1410, Pharmacia, Finland) with internal spectrum library. $^{45}$Calcium incorporation into newly formed bone, muscle and femur was calculated by DPM/mg tissue respectively. A pair of samples was recovered in each group, fixed with 70% cooling ethanol and embedded in methylmetacrylate (MMA). An undemineralized section 10 μm thick was made using a cutting-grinding method (Exakt-Apparatebau, Hamburg, Germany) and stained with toluidine blue for light microscopic analysis. GLM-ANOVA and Scheffe's test were used for statistical analysis. Significant difference was defined at the level of $p<0.01$.

Experiment 5

Results

Characterization and Bioactivity of Moose BMP

HPLC chromatography established that the partially purified mBMP preparation was a multimer with molecular weight ranging from 11–700 kD. The dominant components comprised low-molecular-weight polypeptide fractions of 11 to 40 kD in the spectrum (FIG. 2). The ectopic bone inductive, capacity of the moose BMP was confirmed radiographically and histologically at 10 and 21 days after implantation. New bone formation in the muscle pouch was radiologically detectable at a dose as low as 2.0 mg of partially purified moose BMP. As the dose increased from 0.5–15 mg, the amount of newly formed bone was clearly augmented. Histological analysis showed that newly formed bone was composed mainly of normal hypertrophic cartilage and woven bone with marrow tissue.

Experiment 6

$^{45}$Ca Incorporation $^{45}$Ca incorporation in the different test groups with composite implants was notably superior to the controls of collagen-BMP, BMP, natural coral-collagen, tricalcium phosphate-collagen, natural coral and tricalcium phosphate alone. The highest peak of $^{45}$Ca incorporation took place in natural coral-collagen-BMP composite with high-dose moose BMP (28.06±2.83 DPM/mg/tissue) at the 10th day. It was significantly higher than tricalcium phosphate-collagen-BMP composite (19.45±3.05 DPM/mg tissue), collagen-BMP and BMP (6.09±0.43 and 5.6±0.24 DPM/mg tissue) in high-dose moose BMP at the 10th day respectively.

The same trend was observed in the groups with high-dose moose BMP at the 20th day and with low-dose moose BMP at both the 10th and 20th day. Compared to corresponding groups at the 10th day, significantly lower incorporations of $^{45}$Ca were noted in the composite implant, collagen-BMP and BMP groups at the 20th day. Discrepancies were also demonstrated between the paired composite implants with identical components in high-dose and in low-dose moose BMP at the same observation times ($p<0.01$). $^{45}$Ca incorporation in different ceramic controls was more or less close to the level of the muscle. However, higher $^{45}$Ca incorporation in natural coral with or without collagen was observed that in tricalcium phospahte with or without collagen at the 10th day as against the 20th day (FIG. 3).

There were no significant difference in $^{45}$Ca incorporation into the muscles or femurs between moose BMP implanted and non-implanted mice, and between the 10th and 20th day. Implanting moose BMP in a local muscle pouch did not apparently affect systemic calcium metabolism.

Experiment 7

Radiological and Histological Evaluation

Compatible with the $^{45}$Ca tracing results, visible ectopic osteoinduction was radiologically displayed in composite implants, collagen-BMP and BMP groups, but not in all ceramic controls with or without collagen at the 10th and 20th day after implantation. Newly formed bone surrounded and bordered the ceramic discs which showed a sharp contrast against the shadow of muscle in X-ray films. Twenty days after implantation, the amount and density of newly formed bone were clearly reduced compared to those in corresponding groups at 10 days. Osteoinductive rates in different groups and times are shown in Table 2. Histological analysis revealed that newly formed bone comprised mostly patches of normal woven bone and cartilage was dispersed around and deposited into the pores of the ceramic discs in composite implants. More new bone and cartilage formed in 10 days than in 20 days. Some woven bone and cartilage were fragmented and many karyocytes infiltrated in the sections 20 days after implantation. Negative bone formation and proliferation of fibrous tissue without apparent karyocyte infiltration were observed in the BMP-free controls.

Experiment 8

Bone Induction and Healing in Sheep

Diaphyseal segmental defects of tibia in eighteen sheep were used to evaluate the potential of bone induction and healing by a composite bone substitute comprising tricalcium phosphate cylinder impregnated with naturally occurring sheep BMP and Type IV collagen. The composite bone substitutes were charged with a low dose 13 mg and high dose 100 mg sheep BMP respectively. The tricalcium phosphate cylinders impregnated with type IV collagen alone tricalcium phosphate cylinders were used as control. In accordance with dose-dependent bone induction of sheep BMP, a significantly larger area and more highly integrated intensity of newly-formed external callus between high dose composite bone substitute and low dose composite bone substitute or tricalcium phosphate cylinders was quantified using computerized image analyser at both 3 and 6 weeks. The torsional test showed that the maximal torque capacity, the maximal angular deformation, absorption of energy and bone stiffness of healed osteotomized tibia with implants recovered 49–80% in tricalcium phosphate cylinders, 72–109% in low dose composite bone substitute and 117–175% in high dose composite bone substitute against the corresponding contralateral tibia at 16 weeks. A significantly increased bone stiffness was present in high dose composite bone substitute against low dose composite bone substitute. Imbued with osteoinductivity, osteoconductivity and mechanical strength, the composite cone substitute defined in this study is more accessible for clinical application.

Experiment 9

Surgical Procedures

A tibial segmental defect model was used to evaluate bone healing in eighteen adult sheep, 14 female and 4 male, with an average body weight of 44.11±6.35 kg. They were kept in sheep pens for 4–7 days before the operation.

Anaesthesia was induced by Propolol (2 mg/kg) and maintained by 2–2.5% Halothane in oxygen in a semiclosed ventilation system after incubation. Under sterile conditions, the right tibia was exposed by medial approach. The proximal and distal screw holes of the plate were predrilled and tapped prior to resection of the midshaft. Segmental unilateral defects standardized to 16 mm in length were created with a Gigli saw subperiosteally. After thorough irrigation of the operating field, the defects were replaced by 6 low dose composite bone substitute, and 6 tricalcium phosphate cylinders implants respectively. The implant was firmly secured in the defect through the plugs at each end inserted in the medullary canal. The osteotomized tibia was immobilized by two overlapping contoured autocompression plates, 4 mm thick, 8 and 6 holes respectively and cortical screws on the medial side of the tibia. The muscles and skin were closed in layers. One dose of Benzylpenicillin (66,000 I.U.) intravenously one hour preoperatively and Procaine penicillin (36,000 I. U.) intramuscularly per day for 4 consecutive postoperative days were administered to each sheep to protect from infection. The animals were allowed to walk unrestricted immediately after surgery.

Experiment 10

Image Quantitation

Sequential craniocaudal and lateromedial X-ray views of the osteotomized tibia were taken at 3, 6, 12 and 16 weeks after surgery. All radiograms obtained from 3 to 12 weeks were scanned by a computerized optical density scanner of the Bio Image System (6 XRS, Millipore Corporation, USA), which was connected to a Sunspark Station EIPX and analyzed with 2D system software to follow quantitative changes in area and integrated intensity bounded on craniocaudal and lateromedial images of each sample was standardized to one fourth of the total area and integrated intensity of callus respectively. The unit was defined as $mm^2$ in area and optical density in integrated intensity. After removal of soft tissue and the plates, the sheep tibia were tomographed by computerized tomography (CT) in consecutive axial sections of 3 mm interval to quantify the average cross-sectional area and density of callus. The density was expressed in Hunsfield Units (10)

Experiment 11

Mechanical Testing

All harvested tibias from both sides were kept moist with physiological saline, sealed in plastic bags separately and frozen in −20° C. till the mechanical test.

Mechanical testing was performed using a modified torsion test machine (Lepola et al., Clin. Orthop. 297, 55–61, 1993). A constant angular speed of 6.5 degrees per second was preset according to the study by Strömberg et al. (Acta Orthop. Scand. 47, 257–263, 1976). The machine includes electronic circuity for a strain gauge excitation and torque measurement. The non-rotating end of the machine was equipped with a torque sensor based on strain gauge. The maximal load capacity of the machine was 250 Nm. Total machine errors were below 1%. The torsional load curves were registered by a plotter.

Thawed in room temperature for 4 hours, both ends of the tibia were trimmed and embedded in nonsymmetrical circular aluminium molds using polyester resin. Mold orientation and bone centralization were maintained with a specially designed mold supporter.

The torsional arm was defined as 135 mm. The specimens were saturated with saline during preparation and testing. The torsion test was carried out by loading at an angular velocity of 6.5 degrees per second until the tibia reached fracture point. The contralateral tibia in which corresponding holes had been made was used as a paired control against the osteotomized one.

The percentage of maximal torque capacity (MTC), maximal angle of deformation (MA), absorption of energy (AE) and bone stiffness (BS) in the osteotomized tibia against the contralateral one was calculated.

According to a pilot test with intact sheep tibia the standard errors of the method were as follows:

MTC 4.7%, MA 8.4%, BS 8.6% and AE 13.1%. The sites of the fracture lines were recorded and compared between the tibia implanted with composite bone substitutes and with tricalcium phosphate cylinders.

Experiment 12

Histology

After the mechanical test, the block of the specimen including the implanted materials was sawn transversely into slices 0.4–2.0 mm thick using a diamond band saw (Accutome 5, Struers Tech A/S, Copenhagen, Denmark), fixed immediately in 10% neutral formalin and embedded in methylmetacrylate. An undemineralized histological section 12–20 μm thick was prepared using a cutting and grinding method and stained with Van Gieson for light-microscopic analysis.

Experiment 13

Statistical Analysis and Results

The GLM-ANOVA variance analysis program and Duncan's multiple comparison test were used for the statistical analysis of all quantitative data. Significance was considered at $p<0.05$.

During the experimental period one sheep in the tricalcium phosphate-collagen group was excluded at 5 weeks because of a split fracture of the distal stump of the osteotomized tibia and loss of immobilization. One sheep with a low dose of sheep BMP was sacrificed because of exposure of the plates and infection of the osteomized site at 8 weeks after surgery. Sixteen sheep completed the study at the end of 16 weeks.

Experiment 14

Image Analysis

Visible callus formation around the implants was radiographically demonstrated in all groups 3 weeks after surgery. The extent of callus grown and reached the maximum at 6 weeks then decreased from 12 to 16 weeks. The radiodensity of callus was gradually augmented from 3 to 16 weeks. New bone was apposited surrounding osteotomized sites except for the side under the plate. Newly-formed bridging callus was locally domed around composite bone substitute groups rather than distributed longitudinally underneath the periostenum in the tricalcium phosphate cylinders group.

Computerized image analysis showed that the area and integrated intensity of the bridging callus were much higher in composite bone substitute supercharged with 100 mg sheep BMP than in composite bone substitute with 13 mg sheep BMP or tricalcium phosphate cylinders from 3 to 12 weeks after implantation. Significant differences in the area and integrated intensity of the callus were noted between the three groups and at different weeks.

At the termination of the experiment, good osteointegration between newly-formed callus and implants was observed in the cross-sections of the computerized tomography (CT) scan. There was no apparent demarcation between the implants and the bridging callus. Compatible with the computerized image analysis, the discrepancy in average density of callus in axial consecutive sections of CT scan was significant between different groups at 16 weeks. However, no simultaneous significant difference in area of callus was shown between the different groups (Table 3).

The biodegradation of tricalcium phosphate cylinders were observed radiographically and tomographically with CT-scanning. The tricalcium phosphate cylinder resorption took place in the circumference and along the inner wall of the central hole of the cylinder from 6 weeks after implantation. Some of the tricalcium phosphate cylinders fragmented and some remained intact to the end of experiment. More degradation of the tricalcium phosphate cylinder seemed to occur in the composite bone substitute than the tricalcium phosphate-collagen group.

TABLE 3

The Average Sectional Area and Density of Callus on the CT Scanning Film at 16 Weeks After Implantation

| — | Area(cm$^2$) | Density(HU) |
|---|---|---|
| TCPC | 1.94 ± 0.91 | 1258.36 ± 201.43 |
| CBSL | 3.51 ± 1.48 | 1036.84 ± 149.85 |
| CBSH | 2.93 ± 0.80 | 1401.32 ± 75.95 |
| p-value< | 0.21 | 0.01* |

*Significant difference (GLM-ANOVA analysis).

Experiment 15

Mechanical Test

The data on the torsion test are summarized in Table 4.

The maximal torque capacity, maximal angular deformation of failure, absorption of energy and bone stiffness of osteotomized tibia with implants recovered 49–80% in tricalcium phosphate-collagen, 72–109% in low dose composite bone substitute and 117–175% in high dose composite bone substitute as against the corresponding contralateral tibia at 16 weeks. Compared to the tricalcium phosphate-collagen control, the increased mechanical parameters were seen in the low dose composite bone substitute and high dose composite bone substitute groups.

In the high dose composite bone substitute group all parameters of the healed tibia were even over the contralateral one with coincident holes. The mean percentage values in bone stiffness showed a significant difference of high dose composite bone substitute from tricalcium phosphate-collagen or low dose composite bone substitute but no significant difference between tricalcium phosphate-collagen and low dose composite bone substitute when compared using GLM-ANOVA and Duncan's multiple comparison test.

TABLE 4

Mechanical Test Parameters in Sheep Segmental Tibial Defects Implanted with TCPC, CBSL and CBSH at 16 Weeks

| Parameters | | TCPC (5) | CBSL(13 mgBMP) (5) | CBSH(100 mgBMP) (6) |
|---|---|---|---|---|
| MTC (Nm) | (Implant) | 21.8 ± 1.57 | 24.33 ± 6.93 | 31.96 ± 9.87 |
| | (Control) | 32.9 ± 7.21 | 33.53 ± 13.60 | 27.58 ± 10.56 |
| | % control | 63.22 ± 18.98 | 72.53 ± 43.19 | 137.73 ± 86.92 |
| | p-value between CBSH and CBSL or TCPC <0.13 | | | |
| MA (degree) | (Implant) | 12.85 ± 3.30 | 14.34 ± 0.74 | 14.17 ± 2.35 |
| | (Control) | 17.79 ± 2.10 | 13.89 ± 5.01 | 13.03 ± 3.91 |
| | % control | 70.22 ± 19.36 | 109.52 ± 46.77 | 117.92 ± 37.49 |
| | p-value between CBSH and CBSL or TCPC <0.10 | | | |
| AE (Nm. degree) | (Implant) | 133.52 ± 31.22 | 185.04 ± 44. | 218.59 ± 83.54 |
| | (Control) | 270.26 ± 82.48 | 251.84 ± 75.07 | 198.77 ± 98.10 |
| | % control | 49.29 ± 27.02 | 86.28 ± 48.10 | 175.65 ± 101.07 |
| | p-value between CBSH and CBSL or TCPC <0.33 | | | |
| BS (Nm/degree) | (Implant) | 2.01 ± 0.49 | 2.22 ± 0.58 | 2.76 ± 0.85 |
| | (Control) | 2.18 ± 0.34 | 2.45 ± 0.42 | 2.21 ± 0.41 |
| | % control | 80.60 ± 19.26 | 94.41 ± 22.71 | 125.49 ± 33.91 |
| | p-value between CBSH and CBSL or TCPC <0.04* | | | |

*Significant difference (GLM-ANOVA analysis).

All specimens failed in a spiral fracture pattern consistent with the torsional force loaded. The fracture line through the implant-bone contact interface occurred in 2 out of 5 tricalcium phosphate cylinders, 2 out of 5 low dose composite bone substitute and one out of 6 high dose composite bone substitute.

Experiment 16

Histology

New bone formation could be seen in the inner pore, interconnected channels and periphery of the tricalcium phosphate cylinder charged with or without sheep BMP. The well-remodelled lamellar bone was morphologically normal and no inflammatory cells infiltrated around the implants in either the composite bone substitute and tricalcium phosphate-collagen group at 16 weeks. More advanced remodelled new bone was revealed in composite bone substitute charged with a low or high dose of sheep BMP. The areas of remodelled bone adjacent to central holes in the tricalcium phosphate cylinders seemed to be colonized by normal bone marrow cells. There was no interposed fibrous tissue on the interface between newly formed bone and tricalcium phosphate cylinder. More absorption and dissolution of tricalcium phosphate cylinders was seen near the endoperiosteal callus and medullary canal in the composite bone substitute than in the tricalcium phosphate-collagen group.

In conclusion, the composite bone substitute with triple components provided the advantages of osteoinduction, osteoconduction and mechanical resistance. Nowadays advances in biomaterials research have provided better possibilities to screen for an appropriate biomaterial as skeleton for composite bone substitute. The limited sources and impurity of naturally occurring BMP could be circumvented by the preparation of recombinant BMP. With the development of reconstitution techniques, a desirable composite bone substitute for replacing autogeneic or allogeneic grafts for human being will be available. The most substantial relevance in this experimental study was to highlight the necessity and advantages of developing a synthetic bioactive bone substitute for medical practice.

Experiment 17

Bone Induction and Healing in Human Beings

A clinical test is started in March 1996. In said clinical test composite material composed of biocoral-bovine BMP and tricalcium phosphate-bovine BMP will be used for treating patients with bone fractures which show difficulties in healing. The composite materials are prepared as indicated above and the tests to be performed are essentially the same as described above.

What we claim:

1. A method for preparing a bone morphogenetic protein complex comprising:
   (a) extracting protein from bone material with guanidinium hydrochloride (GuHCl);
   (b) concentrating the extract by filtering with a tangential flow system and/or a ultrafiltration system;
   (c) performing at least one dialysis of the concentrated extract against water or a buffer solution and dissolving insoluble material in buffered urea;
   (d) performing a HPLC gel filtration of the buffered urea dissolved material to fractionate the protein material into three fractions, fraction I having a molecular weight of 100–700 kD, fraction II, having a molecular weight of 25–55 kD, and a fraction III having a molecular weight of 15–25 kD; and
   (e) drying and sterilizing fraction I.

2. The method of claim 1, further comprising combining fractions I and III and drying and sterilizing said fractions.

* * * * *